(12) United States Patent
Popp et al.

(10) Patent No.: US 9,126,372 B2
(45) Date of Patent: *Sep. 8, 2015

(54) METHOD OF MANUFACTURING A BODY ADHERING ABSORBENT ARTICLE ORIENTATED IN THE CROSS-MACHINE DIRECTION WITH REDUCED CURL

(71) Applicant: Kimberly-Clark Worldwide, Inc., Neenah, WI (US)

(72) Inventors: Robert Lee Popp, Greenville, WI (US); Jay David Gottleib, Oshkosh, WI (US); Joseph Daniel Coenen, Kaukauna, WI (US); Gary Alan Turchan, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/276,630

(22) Filed: May 13, 2014

(65) Prior Publication Data

US 2014/0326390 A1 Nov. 6, 2014

Related U.S. Application Data

(63) Continuation of application No. 13/022,706, filed on Feb. 8, 2011, now Pat. No. 8,758,547.

(51) Int. Cl.
*B32B 37/00* (2006.01)
*A61F 13/15* (2006.01)
(Continued)

(52) U.S. Cl.
CPC ......... *B29C 65/741* (2013.01); *A61F 13/15699* (2013.01); *A61F 13/15723* (2013.01);
(Continued)

(58) Field of Classification Search
CPC ............... Y10T 156/1052; Y10T 156/1084; B32B 2555/02; A61F 13/15699; A61F 13/82
USPC .......... 156/160, 163, 164, 183, 229; 604/389, 604/390
See application file for complete search history.

(56) References Cited

U.S. PATENT DOCUMENTS 2,720,477 A 10/1955 Lancaster
2,862,846 A 12/1958 Blackford et al.
(Continued)

FOREIGN PATENT DOCUMENTS

EP 0 638 303 B1 11/1997
EP 0 850 628 A1 7/1998
(Continued)

OTHER PUBLICATIONS

American Society for Testing Materials (ASTM) Designation: D1300-53 T, "Tentative Specifications and Methods of Test for Laminated Thermosetting Decorative Sheets," pp. 148-166, issued 1953.

(Continued)

*Primary Examiner* — Carson Gross
(74) *Attorney, Agent, or Firm* — Kimberly-Clark Worldwide, Inc.

(57) ABSTRACT

The present disclosure provides a method of manufacturing body adhering absorbent articles orientated in the cross-machine direction, body adhering absorbent article having reduced or eliminated curl. The articles are manufactured with reduced curl by selectively reducing or eliminating the shell elastic tension in regions where components of the body adhering absorbent article are to be attached to form the composite absorbent article web. In certain aspects the body adhering absorbent articles are manufactured by supplying an elastic web of shell material having a longitudinal and transverse direction, that is stretchable only in the transverse direction, attaching at least one component to form a composite web material, and cutting the composite web material to form a body adhering absorbent article.

20 Claims, 13 Drawing Sheets

(51) Int. Cl.
*B29C 65/74* (2006.01)
*A61F 13/82* (2006.01)
*B32B 37/12* (2006.01)
*B32B 38/00* (2006.01)
*B32B 38/06* (2006.01)
*B29L 31/48* (2006.01)

(52) U.S. Cl.
CPC ..... *A61F13/15739* (2013.01); *A61F 13/15764* (2013.01); *A61F 13/15804* (2013.01); *A61F 13/82* (2013.01); *B29C 65/74* (2013.01); *B32B 37/1292* (2013.01); *B32B 38/0004* (2013.01); *B29L 2031/4878* (2013.01); *B32B 38/0008* (2013.01); *B32B 38/06* (2013.01); *B32B 38/145* (2013.01); *B32B 2309/02* (2013.01); *B32B 2309/04* (2013.01); *B32B 2310/028* (2013.01); *B32B 2555/02* (2013.01); *Y10T 156/108* (2015.01); *Y10T 156/1052* (2015.01)

(56) References Cited

U.S. PATENT DOCUMENTS

| | | | |
|---|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,531,847 A | 10/1970 | Wallerstein |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 4,414,970 A | 11/1983 | Berry |
| 4,488,928 A | 12/1984 | Ali et al. |
| 4,556,441 A | 12/1985 | Faasse, Jr. |
| 4,631,062 A | 12/1986 | Schultz et al. |
| 4,655,210 A | 4/1987 | Edenbaum et al. |
| 4,693,858 A | 9/1987 | Volke |
| 4,743,245 A | 5/1988 | Schultz et al. |
| 4,804,380 A | 2/1989 | Lassen et al. |
| 4,846,824 A | 7/1989 | Schultz et al. |
| 4,991,378 A | 2/1991 | Dotta |
| 5,059,189 A | 10/1991 | Cilento et al. |
| 5,114,419 A | 5/1992 | Daniel et al. |
| 5,147,338 A | 9/1992 | Lang et al. |
| 5,147,938 A | 9/1992 | Kuller |
| 5,194,550 A | 3/1993 | Rance et al. |
| 5,382,400 A | 1/1995 | Pike et al. |
| 5,445,627 A | 8/1995 | Mizutani et al. |
| 5,453,143 A * | 9/1995 | Menard ........................ 156/204 |
| 5,501,661 A | 3/1996 | Cartmell et al. |
| H1602 H | 10/1996 | Brock |
| 5,611,790 A | 3/1997 | Hines et al. |
| 5,618,281 A | 4/1997 | Betrabet et al. |
| 5,658,270 A | 8/1997 | Lichstein |
| 5,662,633 A | 9/1997 | Doak et al. |
| 5,685,833 A | 11/1997 | Turngren |
| 5,759,560 A | 6/1998 | Dillon |
| 5,807,367 A | 9/1998 | Dilnik et al. |
| 5,967,009 A | 10/1999 | Truttmann et al. |
| 6,001,471 A | 12/1999 | Bries et al. |
| 6,004,253 A | 12/1999 | Riedel et al. |
| 6,045,900 A | 4/2000 | Haffner et al. |
| 6,156,818 A | 12/2000 | Corzani et al. |
| 6,169,224 B1 | 1/2001 | Heinecke et al. |
| 6,174,399 B1 | 1/2001 | Decandia et al. |
| 6,177,482 B1 | 1/2001 | Cinelli et al. |
| 6,187,989 B1 | 2/2001 | Corzani et al. |
| 6,191,189 B1 | 2/2001 | Cinelli et al. |
| 6,211,263 B1 | 4/2001 | Cinelli et al. |
| 6,213,993 B1 | 4/2001 | Zacharias et al. |
| 6,264,784 B1 | 7/2001 | Menard et al. |
| 6,279,440 B1 | 8/2001 | Truttmann et al. |
| 6,298,760 B1 | 10/2001 | Truttmann et al. |
| 6,305,260 B1 | 10/2001 | Truttmann et al. |
| 6,316,524 B1 | 11/2001 | Corzani et al. |
| 6,362,389 B1 | 3/2002 | McDowall et al. |
| 6,365,645 B1 | 4/2002 | Cinelli et al. |
| 6,369,126 B1 | 4/2002 | Cinelli et al. |
| 6,383,431 B1 | 5/2002 | Dobrin et al. |
| 6,620,143 B1 | 9/2003 | Zacharias et al. |
| 6,632,210 B1 | 10/2003 | Glasgow et al. |
| 6,641,569 B1 | 11/2003 | Coles et al. |
| 6,657,009 B2 | 12/2003 | Zhou |
| 6,670,402 B1 | 12/2003 | Lee et al. |
| 6,700,033 B1 | 3/2004 | Marcussen et al. |
| 6,765,123 B2 | 7/2004 | De Jong et al. |
| 6,960,275 B2 | 11/2005 | Vesley et al. |
| 6,977,324 B2 | 12/2005 | Serrano |
| 6,997,915 B2 | 2/2006 | Gell et al. |
| 7,045,559 B2 | 5/2006 | Yahiaoui et al. |
| 7,053,131 B2 | 5/2006 | Ko et al. |
| 7,122,022 B2 | 10/2006 | Drevik |
| 7,125,401 B2 | 10/2006 | Yoshimasa |
| 7,166,179 B2 | 1/2007 | Muesch et al. |
| 7,217,259 B2 | 5/2007 | McDaniel |
| 7,265,158 B2 | 9/2007 | Risen, Jr. et al. |
| 7,351,297 B2 | 4/2008 | Middlesworth et al. |
| 7,358,282 B2 | 4/2008 | Krueger et al. |
| 7,378,450 B2 | 5/2008 | Erkey et al. |
| 7,396,975 B2 | 7/2008 | Sigurjonsson et al. |
| 7,488,186 B1 | 2/2009 | Hayakawa |
| 7,745,682 B2 | 6/2010 | Sigurjonsson et al. |
| 8,758,547 B2 * | 6/2014 | Popp et al. ..................... 156/324 |
| 2004/0116883 A1 | 6/2004 | Krautkramer et al. |
| 2004/0151930 A1 | 8/2004 | Rouns et al. |
| 2005/0010185 A1 | 1/2005 | Mizutani et al. |
| 2005/0065491 A1 | 3/2005 | Schneider et al. |
| 2005/0148984 A1 | 7/2005 | Lindsay et al. |
| 2005/0198931 A1 | 9/2005 | Cesiro et al. |
| 2006/0058764 A1 | 3/2006 | Bohlen et al. |
| 2006/0148917 A1 | 7/2006 | Radwanski et al. |
| 2006/0161125 A1 | 7/2006 | Bohlen et al. |
| 2006/0264884 A1 | 11/2006 | Carstens |
| 2007/0100313 A1 | 5/2007 | Luizzi |
| 2007/0124850 A1 | 6/2007 | Buettner |
| 2007/0179418 A1 | 8/2007 | Ritzdorf et al. |
| 2007/0287973 A1 | 12/2007 | Cohen et al. |
| 2008/0004584 A1 | 1/2008 | Langdon et al. |
| 2008/0015535 A1 | 1/2008 | Gannon et al. |
| 2008/0057811 A1 | 3/2008 | Yahiaoui et al. |
| 2008/0207779 A1 | 8/2008 | Yahiaoui et al. |
| 2008/0241541 A1 | 10/2008 | Conrad et al. |
| 2009/0036858 A1 | 2/2009 | Van Den Bogart et al. |
| 2009/0054864 A1 | 2/2009 | Lira et al. |
| 2009/0062762 A1 | 3/2009 | Himbergen et al. |
| 2009/0069771 A1 | 3/2009 | Yu et al. |
| 2009/0069780 A1 | 3/2009 | Plentovich et al. |
| 2009/0171309 A1 | 7/2009 | Vandenbogart et al. |
| 2009/0182296 A1 | 7/2009 | Dennis et al. |
| 2009/0198203 A1 | 8/2009 | Lira et al. |
| 2009/0204090 A1 | 8/2009 | Dennis et al. |
| 2009/0204092 A1 | 8/2009 | Loyd et al. |
| 2010/0057034 A1 * | 3/2010 | Dennis et al. ............ 604/385.05 |
| 2010/0121304 A1 | 5/2010 | Zhou et al. |
| 2010/0152693 A1 | 6/2010 | Lira et al. |
| 2010/0198177 A1 | 8/2010 | Yahiaoui et al. |
| 2012/0199268 A1 | 8/2012 | Popp et al. |

FOREIGN PATENT DOCUMENTS

| | | |
|---|---|---|
| EP | 1 696 853 B1 | 10/2009 |
| GB | 2 284 767 A | 6/1995 |
| JP | 04-279159 A | 10/1992 |
| WO | WO 95/16424 A1 | 6/1995 |
| WO | WO 98/27910 A1 | 7/1998 |
| WO | WO 98/27912 A1 | 7/1998 |
| WO | WO 98/27913 A1 | 7/1998 |
| WO | WO 98/27915 A1 | 7/1998 |
| WO | WO 98/27916 A1 | 7/1998 |
| WO | WO 98/27917 A1 | 7/1998 |

(56) References Cited

FOREIGN PATENT DOCUMENTS

| | | |
|---|---|---|
| WO | WO 98/27918 A1 | 7/1998 |
| WO | WO 98/28015 A1 | 7/1998 |
| WO | WO 98/28017 A1 | 7/1998 |
| WO | WO 98/28019 A1 | 7/1998 |
| WO | WO 98/28022 A1 | 7/1998 |
| WO | WO 98/28023 A1 | 7/1998 |
| WO | WO 98/55065 A1 | 12/1998 |
| WO | WO 99/01094 A1 | 1/1999 |
| WO | WO 99/01095 A1 | 1/1999 |
| WO | WO 00/00235 A1 | 1/2000 |
| WO | WO 2006/028612 A1 | 3/2006 |

OTHER PUBLICATIONS

"Antiperspirant Drug Products for Over-the-Counter Human Use: Final Monograph," Final Rule, Federal Register—Rules and Regulations, vol. 68, No. 110, Jun. 9, 2003, pp. 34273-34293.

Berner, G. et al. "Photoinitiators-An Overview," Journal of Radiation Curing, vol. 6, No. 2, Apr. 1979, pp. 2-9.

Lloyd, Jillian et al., "Female Genital Appearance: 'Normality' Unfolds," BJOG: An International Journal of Obstetrics and Gynecology, vol. 112, May 2005, pp. 643-646.

Mahdavi, Alborz et al., "A Biodegradable and Biocompatible Gecko-Inspired Tissue Adhesive," PNAS, vol. 105, No. 7, Feb. 19, 2008, pp. 2307-2312.

* cited by examiner

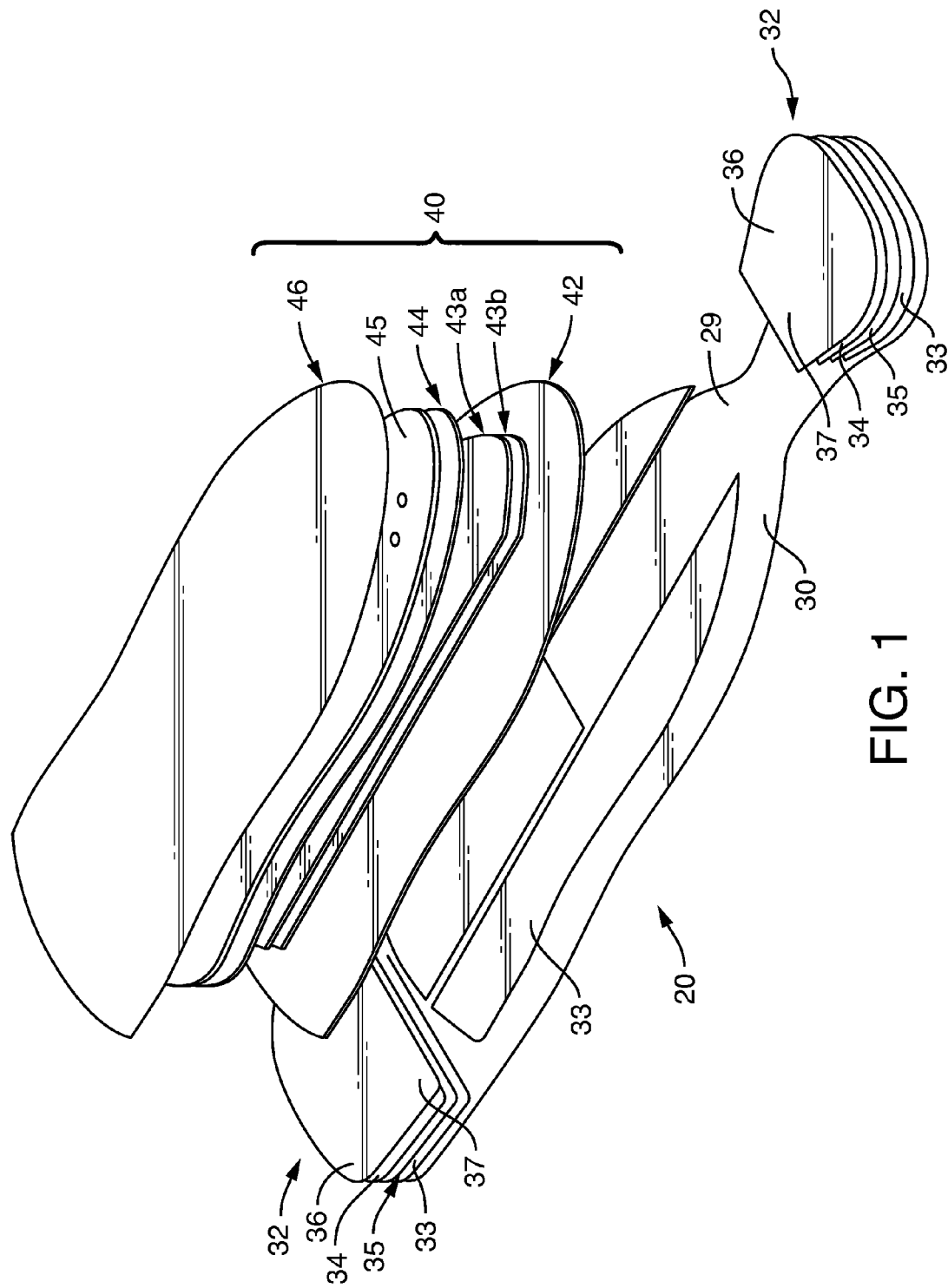

METHOD OF MANUFACTURING A BODY ADHERING ABSORBENT ARTICLE ORIENTATED IN THE CROSS-MACHINE DIRECTION WITH REDUCED CURL

PRIORITY

This application is a continuation of application Ser. No. 13/022,706 entitled METHOD OF MANUFACTURING A BODY ADHERING ABSORBENT ARTICLE ORIENTATED IN THE CROSS-MACHINE DIRECTION WITH REDUCED CURL and filed on Feb. 8, 2011. The entirety of application Ser. No. 13/022,706 is hereby incorporated by reference.

FIELD OF THE INVENTION

This disclosure relates to methods of manufacturing a body adhering absorbent article orientated in the cross-machine direction with little or no curl. Various methods of constructing individual body adhering absorbent articles are described that reduce or eliminate the amount of residual stretch present in the shell where components are attached.

BACKGROUND

Several methods have been proposed for making body adhering absorbent articles. The body adhering absorbent articles generally consist of components which are laminated to an elastic shell, which is generally in a tensioned state during the assembly process, to form a composite web of individual absorbent articles. When the discrete body adhering absorbent articles are die cut from the composite web the individual articles curl toward the elasticized shell material in the areas where it has been attached to the components as a result of residual stretch present in the shell material in the laminated regions.

Curling of a body adhering absorbent article is undesirable because it may interfere with peel strip removal, attachment to the body and the ability of the article to stay attached to the body. Curling of the product in the absorbent area may also interfere with the fit and gasketing of the product. Products which curl are also more difficult to convert, fold, and package increasing the level of defects, and machine downtime.

Accordingly there is a need for a method of manufacturing a body adhering absorbent article that reduces or eliminates the curl of the finished product, thereby enhancing customer satisfaction and easing manufacture.

SUMMARY

It has now been discovered that curl of a body adhering absorbent article may be reduced or eliminated by selectively reducing or eliminating the shell elastic tension in regions where components of the body adhesive absorbent article, such as an adhesive transfer layer component or an absorbent article component, are to be attached to form the composite body adhering absorbent article web. Accordingly, in one aspect the present disclosure provides a method of manufacturing body adhering absorbent articles orientated in the cross-machine direction comprising the steps of supplying a pair of adhesive webs comprising a body attachment adhesive; supplying an elastic shell web having a longitudinal and transverse direction and a pair of opposing peripheral edges extending in the longitudinal direction; attaching the pair of adhesive webs to the opposing peripheral edges of the elastic shell web; attaching at least one absorbent article component to the shell web interior to the opposing peripheral edges to form a composite web material; and cutting the composite web material to form an absorbent article having a predetermined size and shape.

In other aspects the present disclosure provides a method of manufacturing a body adhering absorbent article orientated in the cross-machine direction comprising the steps of supplying an activatable web of shell material having a longitudinal and transverse direction; intermittently activating a portion of the web of shell material in the longitudinal direction to create activated and nonactivated portions of the web of shell material in the lateral direction; attaching at least one component to the at least one nonactivated portion of the web of shell material to form a composite web material; and cutting the composite web material to form an absorbent article having a predetermined size and shape.

In still other aspects the present disclosure provides a method of manufacturing a body adhering absorbent article orientated in the cross-machine direction comprising the steps of supplying a web of shell material having elastic and inelastic zones; attaching at least one component to the inelastic zone of the web of shell material to form a composite web material; and cutting the composite web material to form an absorbent article having a predetermined size and shape.

In yet other aspects the present disclosure provides a method of manufacturing a segmented body adhering absorbent article comprising the steps of supplying two webs of activatable shell material; activating the two webs of shell material; attaching a web comprising an adhesive transfer layer to the two activated webs of shell material; attaching an absorbent component to the two webs of shell material to form a composite web material; and cutting the composite web material to form a segmented body adhesive absorbent article having a predetermined size and shape.

DESCRIPTION OF THE DRAWINGS

FIG. 1 is an exploded view of a body adhesive absorbent article according to one embodiment of the present disclosure;

DEFINITIONS

Figures 2A, 2B:
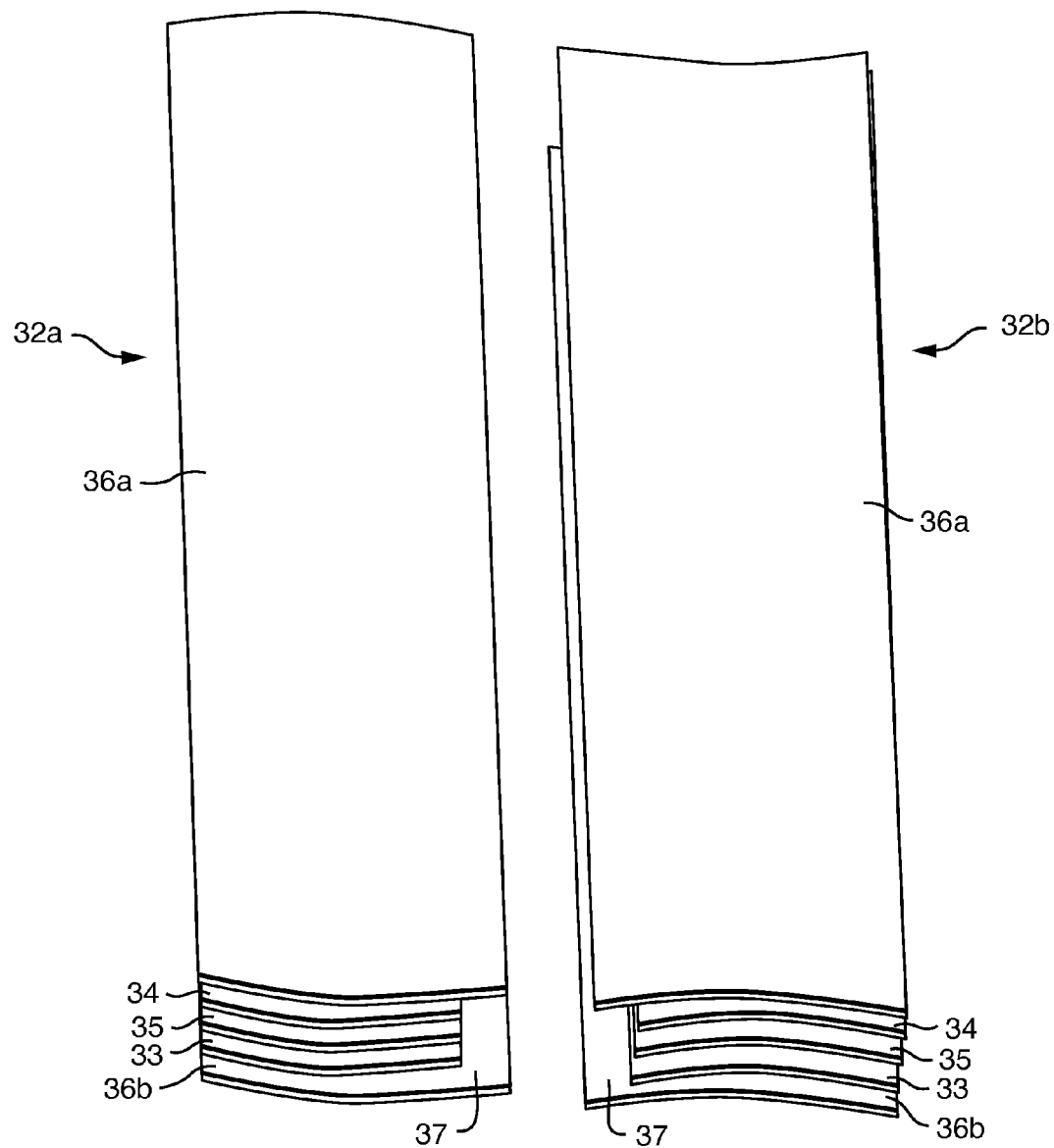
FIGS. 2A and 2B are cross sectional views of adhesive transfer layers according to one embodiment of the present disclosure.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

"Absorbent structure" refers to the central fluid handling portion of an absorbent article and may include but is not limited to one or more of the following components: cellulose fluff, superabsorbent material, coform, absorbent sponge material, surge material, or wicking material but does not include a topsheet or backsheet.

"Absorbent component" may include but is not limited to one or more of the following components: an absorbent structure, as defined above, a fluid pervious topsheet, a fluid impervious backsheet, or attachment adhesive.

As used herein, the term "adhesive transfer layer" generally refers to an adhesive region of the body adhering absorbent article that facilitates adhesion of the article to a user. In certain preferred embodiments the adhesive transfer layer comprises a lower peel strip, construction adhesive, a body attachment adhesive, a nonwoven carrier and an upper peel strip.

As used herein, the term "attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or a refastenable attachment. In addition, the attachment can be completed either during the manufacturing process or by the end wearer.

As used herein, "body-facing" means that surface or side of the article which is intended to be disposed toward or placed adjacent to the body of the wearer during ordinary use. The term "garment-facing" means that surface or side that is on the opposite side of the article from the body-facing surface or side. The garment-facing surface is an outward surface of the article and is intended to be disposed to face away from the wearer's body during ordinary use. The garment-facing surface is generally arranged to face toward or placed adjacent to the wearer's undergarments or clothing when the article is worn.

As used herein, the term "connected" is intended to mean directly connected and indirectly connected. By directly connected, it is intended that the connected elements are in contact with one another or affixed to one another. By indirectly connected, it is intended that one or more intervening or intermediate elements are between the two elements which are secured or "connected" together. The intervening elements may be affixed.

As used herein, the terms "elastomeric," "elastic," "elasticized," and "elastically" generally refer to that property of a material or composite by virtue of which it tends to recover its original size and shape after removal of a force causing a deformation. An elastomeric material is an extendable material having recovery properties. Suitably, an elastically extensible material can be elongated to at least 25% of its relaxed original length (percent elongation refers to the increase in the original length of the untensioned material, i.e., 0% refers to the original length of the untensioned material) in the direction of an applied biasing force, and which will recover, upon release of the applied force, at least 10% of its elongation. It is generally preferred that the elastomeric material or composite be capable of being elongated by from at least about 25% of its relaxed original length (i.e., an increase of 25% from its untensioned length) to about 200% of its relaxed original length, for example preferably from at least about 50 to about 100% of its relaxed original length.

As used herein, the phrase "orientated in the cross-machine direction" refers generally to the orientation of the manufactured absorbent article. For example, with reference to FIG. 5, where the longest dimension 94 of the absorbent article is orientated substantially perpendicular to the direction of travel of the web 30, the absorbent article is said to be manufactured in the cross-machine direction and the absorbent article is said to be "orientated in the cross-machine direction." Conversely, where the longest dimension of the absorbent article is orientated substantially parallel to the direction of travel of the web, the absorbent article is said to be manufactured in the "machine direction," or "MD."

"Untensioned" as used herein to describe a web of material does not mean lacking all tension. In order to handle and process moving webs, some moderate amount of tension is needed to hold the web or material in place. Accordingly, an "untensioned" web or material, as used herein, is under enough tension to process the material, but less than that required to cause substantial deformation (e.g., necking) of the material.

DETAILED DESCRIPTION

Generally, the present disclosure relates to methods of manufacturing a body adhering absorbent article orientated in the cross-machine direction with little or no curl. Various methods of constructing individual body adhering absorbent articles are described that reduce or eliminate the amount of residual stretch present in the shell where components, such as an absorbent article or an adhesive transfer layer, are attached. Eliminating curl is important for facilitating use of the body adhering absorbent article, particularly in the regions of the article that are adhered to the user. By eliminating curl, both the fit and the function of the body adhering absorbent article may be improved.

Now with reference to FIG. 1, one embodiment of a body adhering absorbent article 20 is illustrated. Body adhering article 20 comprises body adhering shell 29, and an absorbent article component 40. The composition of the body adhering shell 29 may be varied depending upon the method of manufacturing. For example, as described in more detailed below, where the method of manufacturing comprises selectively activating a web by treating one or more selected regions of the web to increase the regions stretchability, the web of shell material may comprise a latent elastic laminate that upon activation may suitably be stretched by at least about 25%, or at least about 100%, or at least about 200%, and may suitably recover at least about 5%, or at least about 15%, or about 25% of the stretched length. Other suitable shell materials are discussed below.

The body adhering shell 29 further comprises a body adhesive, for example an adhesive transfer layer (ATL) 32. A preferred configuration of the ATL 32 is shown in FIGS. 2A and 2B. In this embodiment the ATL 32 is configured with a left and right portion 32a and 32b respectively and consists of lower peel strip 36b, construction adhesive 33, body attachment adhesive 34, nonwoven carrier 35, and upper peel strip 36a. The construction adhesive 33 may be, for example, Easymelt 34-5610 (Nation Starch Chemical Co., Bridgewater, N.J.), the body attachment adhesive 34 may be, for example, BMS gel 4a (Biomed Sciences, Inc., Allentown, Pa.), the nonwoven carrier 35 may be, for example, rayon/polyester Spunlace nonwoven (Biomed Sciences, Inc., Allentown, Pa.) and the peel strip 36 may be, for example, 24KSA final release paper (Tekkote Co., Leonia, N.J.).

In one embodiment an ATL 32 comprising a peel strip 36, body attachment adhesive 34, and nonwoven carrier 35 may be manufactured by providing a web of nonwoven carrier 35, providing a web of peel strip 36a, applying a body attachment adhesive 34 to the peel strip 36a and curing the adhesive 34, for example by treating the adhesive 34 with ultraviolet light. Once the adhesive 34 is cured it is laminated to a nonwoven carrier 35. In a preferred embodiment the body attachment adhesive layer is narrower than the peel strip 36a and may be narrower than peel strip 36a and nonwoven carrier 35. This results in the formation of a user grasping section or finger tab 37 on the lateral side inside edges of ATL webs 32a and 32b. In a particularly preferred embodiment the ATL web 32 is made in a multi-wide configuration, slit into individual lanes and wound onto cores.

In another embodiment an ATL 32 comprising a lower peel strip 36b, construction adhesive 33, nonwoven carrier 35, body attachment adhesive 34, and upper peel strip 36a may be manufactured by providing a web of lower peel strip 36b, providing a web of nonwoven carrier 35, applying a construction adhesive 33 to the nonwoven carrier 35 and laminating the nonwoven carrier 35 and construction adhesive 33 to the lower peel strip 36b. A web of upper peel strip 36a is provided and a body attachment adhesive 34 is applied to upper peel strip 36a and cured. The upper peel strip 36a with cured body attachment adhesive 34 is laminated to the nonwoven carrier 35, construction adhesive 33, and lower peel strip 36b laminate.

In still another embodiment an ATL 32 comprising a lower peel strip 36b, construction adhesive 33, nonwoven carrier 35, body attachment adhesive 34, and upper peel strip 36a may be manufactured by providing webs of lower peel strip 36b and nonwoven carrier 35 which are fed into the process, applying construction adhesive 33 to the nonwoven carrier 35 and laminating the nonwoven carrier 35 and construction adhesive 33 composite to the lower peel strip 36b. A web of upper peel strip 36a is provided and discrete patches of body attachment adhesive 34 are applied to upper peel strip 36a and cured. The upper peel strip 36a with cured discrete patches of body attachment adhesive 34 is laminated to the nonwoven carrier 35, construction adhesive 33, and lower peel strip 36b laminate. In this embodiment the discrete patches of body attachment adhesive layer result in the formation of lateral direction user grasping sections 37. ATL lower peel strip 36b and construction adhesive 33 may or may not be needed depending on the method of making the body adhering absorbent article.

In another embodiment an ATL 32 comprising a lower peel strip 36b, construction adhesive 33, nonwoven carrier 35, body attachment adhesive 34, and upper peel strip 36a may be manufactured by providing webs of nonwoven carrier 35 and peel strip 36a which are fed into the process. The peel strip 36a is c-folded over onto itself forming user grasping section 37. Body attachment adhesive 34 is applied to the peel strip 36a, cured and laminated to the nonwoven carrier 35, construction adhesive, and lower peel strip 36b laminate.

In addition to the shell material 30 and ATL 32, the body adhering absorbent article may comprise an absorbent article component 40, which is generally attached to the first side of the shell material 30. The attachment may be in a permanent manner, meaning that the absorbent article component 40 is generally intended not to be removable by the wearer of the article 20. Alternatively, the absorbent article component 40 may be constructed to be removable by the wearer, meaning that the absorbent article component 40 may be removed and replaced with another absorbent article component 40 by the wearer of the article 20, or be replaced with nothing at all. In some aspects, when the absorbent article component 40 is attached to the shell material 30 in a permanent manner, meaning that the absorbent article component 40 is not intended to be removed by the wearer, various bonding means can be used, such as a construction adhesive 33 for example. Examples of useable construction adhesives 33 include any adhesive which will effectively hold the absorbent article component 40 in place, so as not to be separated from the shell material 30. Commercially available construction adhesives usable in the present invention include, for example, Rextac™ adhesives available from Huntsman Polymers, Houston, Tex. Other means may be used to hold the absorbent article component 40 to the shell material 30 including bonding techniques known in the art, including, but not limited to, pressure bonds, adhesive bonds, cohesive bonds, thermal bonds, ultrasonic bonds, embossing, crimping, entangling, fusing, hook and loop, or the like, and combinations thereof.

Where the absorbent article component 40 is preferably removably attached, the absorbent article component 40 is held in place on the shell material 30 by a means which will allow the wearer to remove the absorbent article component 40. One such means of holding the absorbent article component 40 is by using a pressure sensitive adhesive. Suitable pressure sensitive adhesives include, but are not limited to, any commercially available pressure sensitive adhesive. Examples of suitable pressure sensitive adhesives usable to removably hold the absorbent article component 40 in place on the shell material 30 include pressure sensitive adhesives available from National Starch, Bridgewater, N.J.

In certain embodiments it may be advantageous for the absorbent article component 40 to have a backsheet 42 and more preferably a fluid impervious backsheet. The backsheet can serve to provide liquid impermeability to the absorbent article component 40, such that any fluids entering the absorbent structure 24 will not flow through to the clothing of a wearer. One example of a commercially available fluid impervious backsheet is the XP-3473a baffle available from Huntsman Packaging Corporation, Houston, Tex. The absorbent structure 24 may also comprise wicking layers 43a and 43b, which may be formed from meltblown microfiber such as the 50 gsm meltblown fibers commercially available from Yuhan-Kimberly Ltd., Korea. The absorbent article component 40 further comprises an absorbent layer 44, intake layer 45 and topsheet 46. The absorbent layer 44 may contain one or more layers of absorbent materials, such as fibrous materials and/or superabsorbent materials for example. Each of the layers can contain similar materials or different materials. Materials that can be used to form the absorbent layer 44 include those materials conventionally used in absorbent articles and includes materials, such as, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A desired material is wood pulp fluff, for it is low in cost, relatively easy to form, and has good absorbency.

In a preferred embodiment the body adhering absorbent article 20 comprises a peel strip 36, which may extend in the lateral direction 77 beyond the extent of the body attachment adhesive 34 forming a user grasping section also know as a finger tab 37. The presence of finger tab 37 allows the user to grasp the peel strip by placing their thumb under the unattached peel strip region and grasping the peel strip in the user grasping section 37 between the thumb and forefinger. The user of the product applies a peeling force to remove the anterior and posterior peel strips 36.

Figure 3:
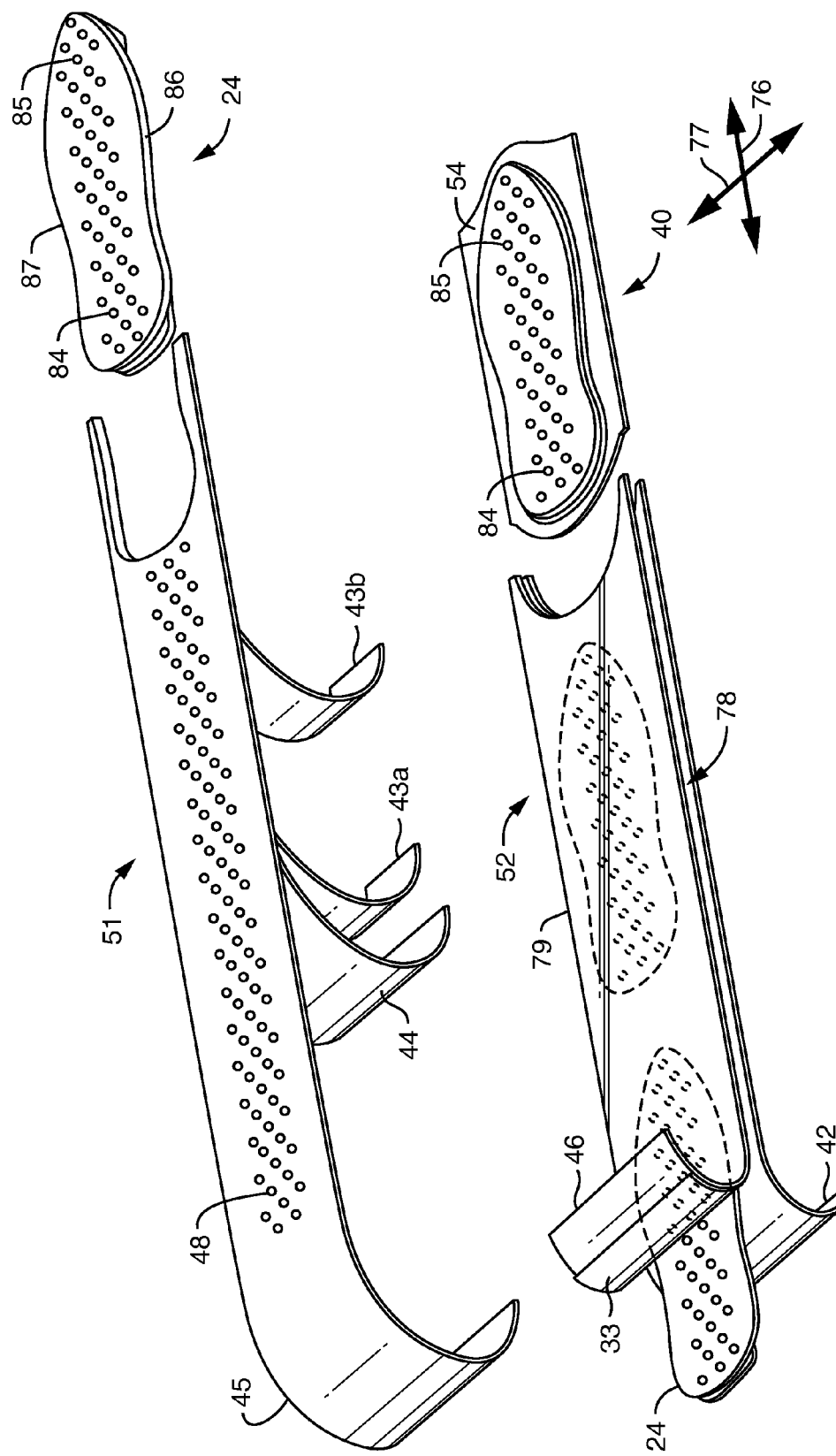
FIG. 3 shows one method of manufacturing an absorbent structure and absorbent article component according to one embodiment of the present disclosure.

Referring to FIG. 3, one method of manufacturing absorbent article components 40 is illustrated. The process has a machine direction 76 and a cross-machine direction 77. The process consists of assembling an absorbent structure web 51, die cutting individual absorbent structures 24 from web 51, adhesively laminating individual absorbent structures 24 between webs of topsheet material 46 and backsheet material 42 forming composite web 52 and die cutting individual absorbent article components 40 from composite web 52. Absorbent article components 40 have an anterior portion 84 and a posterior portion 85. Anterior portion 84 is designed to align with the anterior of the wearer in use and posterior portion 85 is designed to align with the posterior of the wearer in use.

Absorbent structure web 51 may contain one or more layers of absorbent materials, such as fibrous materials and/or superabsorbent materials for example. Each of the layers can contain similar materials or different materials. In a particular embodiment absorbent structure web 51 may be formed by providing an intake layer web 45, creating apertures 48 through intake layer 45, delivering an absorbent web 44 and attaching it to the garment side 89 of intake layer 45, delivering one or more layers of distribution material 43 and attaching the one or more layers to the intake web absorbent web composite forming the completed absorbent structure composite web 51.

Absorbent article composite web may be formed by delivering a series of longitudinally spaced absorbent structures 24 orientated such that the longitudinal center line of each absorbent structure 24 is parallel with the machine direction and where the posterior portions 85 of each absorbent structure 24 in the series are adjacent to the anterior portion 84 of the subsequent absorbent structures 24; delivering a web of backsheet material 42, in a particular embodiment construction adhesive may be applied to the body facing surface of backsheet web 42; and delivering a web of topsheet material 46, in a particular embodiment construction adhesive 33 may be applied to topsheet web 46. The series of absorbent structures 24 are then sandwiched between and attached to at least one of the backsheet web 42 or topsheet web 46 completing the formation of the absorbent article composite web 52. In the preferred embodiment of absorbent article component absorbent structure 24 is not coextensive with the region of topsheet 46 and backsheet 42 adjacent to the peripheral edge of absorbent structure 24 which is laminated together such that when the absorbent article component 40 is cut from web 52 a peripheral edge is formed devoid of absorbent structure 24. The composite web 52 may then be cut to form individual absorbent components 40. In the preferred embodiment absorbent structures 24 are not coextensive with topsheet layer 46 and backsheet layer 42 but have a peripheral edge 54 which seals and contains absorbent structure within a backsheet 42 topsheet 46 envelope.

Topsheet 46 should be able to manage different body excretions depending on the type of product. In feminine care products, often the body-side liner or topsheet 46 must be able to handle menses and urine. In certain embodiments the topsheet 46 may include a layer constructed of any operative material, and may be a composite material. For example, the body-side liner or body-contacting layer can include a woven fabric, a nonwoven fabric, a polymer film, a film-nonwoven fabric laminate or the like, as well as combinations thereof.

Suitable construction adhesives include, for example, Rextac™ adhesives, as well as adhesives available from Bostik Findley, Inc, Wauwatosa, Wis.

Backsheet web 42 may be a fluid impermeable web. Alternately backsheet web 42 can be a fluid pervious web. Backsheet web 42 may, for example, include a polymeric film, a woven fabric, a nonwoven fabric or the like, as well as combinations or composites thereof. For example, the backsheet 42 may include a polymer film laminated to a woven or nonwoven fabric. In a particular feature, the polymer film can be composed of polyethylene, polypropylene, polyester or the like, as well as combinations thereof.

Figure 4:
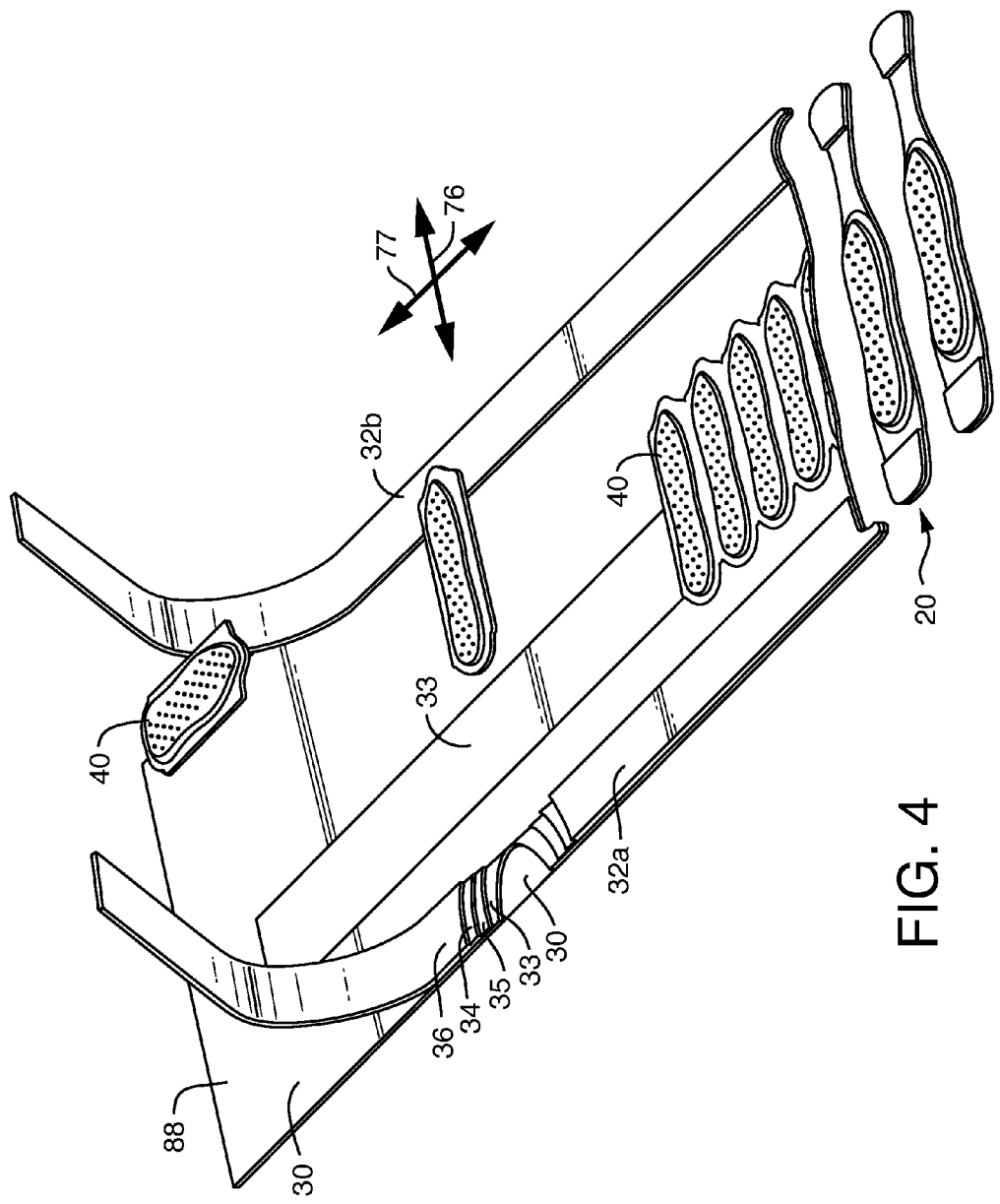
FIG. 4 shows a cross-machine direction method of manufacturing a body adhering absorbent article according to one embodiment of the present disclosure.

With reference to FIG. 4, manufacture of the body adhering absorbent article continues with delivery of the web of a shell material 30 having a body facing side 88 and a garment facing side 89. As noted previously, the shell material 30 can include a polymeric film, a woven fabric, a nonwoven fabric, a foam or the like, as well as combinations or composites thereof. In some aspects, shell material may include a laminate structure, such as a polymer film laminated to a woven or nonwoven fabric. The exact composition of the shell material 30 may vary depending on the method of manufacture, as described more fully below. In certain embodiments the shell web 30 is corona treated to improve its adhesion properties. Alternately shell material 30 can be pre-corona treated. A web of pre-laminated composite 32 referred to as an "Adhesive Transfer Layer" or ATL comprising a carrier sheet 35, body adhesive 34, and peel strip 36 is provided and adhered to the web of shell material 30 to form a shell composite web 53.

Manufacture continues with the preparation of the shell composite web 53 for attachment of absorbent component 40. An initial die cut is made in composite web 53 to remove a portion of material that will be covered by absorbent article component 40. In an alternate embodiment, as illustrated in FIG. 4, die cutting can be eliminated if absorbent articles 40 are positioned within or coextensive with individual body adhering shell 29. An attachment means, such as an adhesive 33, is then applied to the shell composite web 53. In other embodiments the attachment means may be applied to the composite absorbent web 52. Attachment means can be eliminated if the absorbent article component 40 has an attachment means for attaching it to body adhering shell 29. The attachment means can be a one part system, e.g., construction adhesive 33 for attaching absorbent article component 40 to body adhering shell 29. Alternately attachment means can be a two part attachment system, not shown, such as a hook and loop fastener, cohesive, snaps, buttons, etc. where one part of the two part attachment means is located on body adhering shell 29 and the second part of attachment means 21 is located on absorbent article component 40.

Next individual absorbent article components 40 are delivered rotated 90 degrees and attached to body facing surface 88 of composite web 53 such that barrier layer 42 of absorbent article component 40 is adjacent to body facing surface 88 of composite web 53. In this embodiment construction adhesive 33 is used to make the attachment. One skilled in the art however, will appreciate that "attach" refers to any method of joining, adhering, connecting, bonding, sewing together, or the like, of two elements. Two elements will be considered to be attached together when they are integral with one another or attached directly to one another or indirectly to one another, such as when each is directly attached to intermediate elements and include permanent, releasable, or a refastenable attachment. Manufacture continues by die cutting individual body adhering absorbent articles 20.

Figure 5:
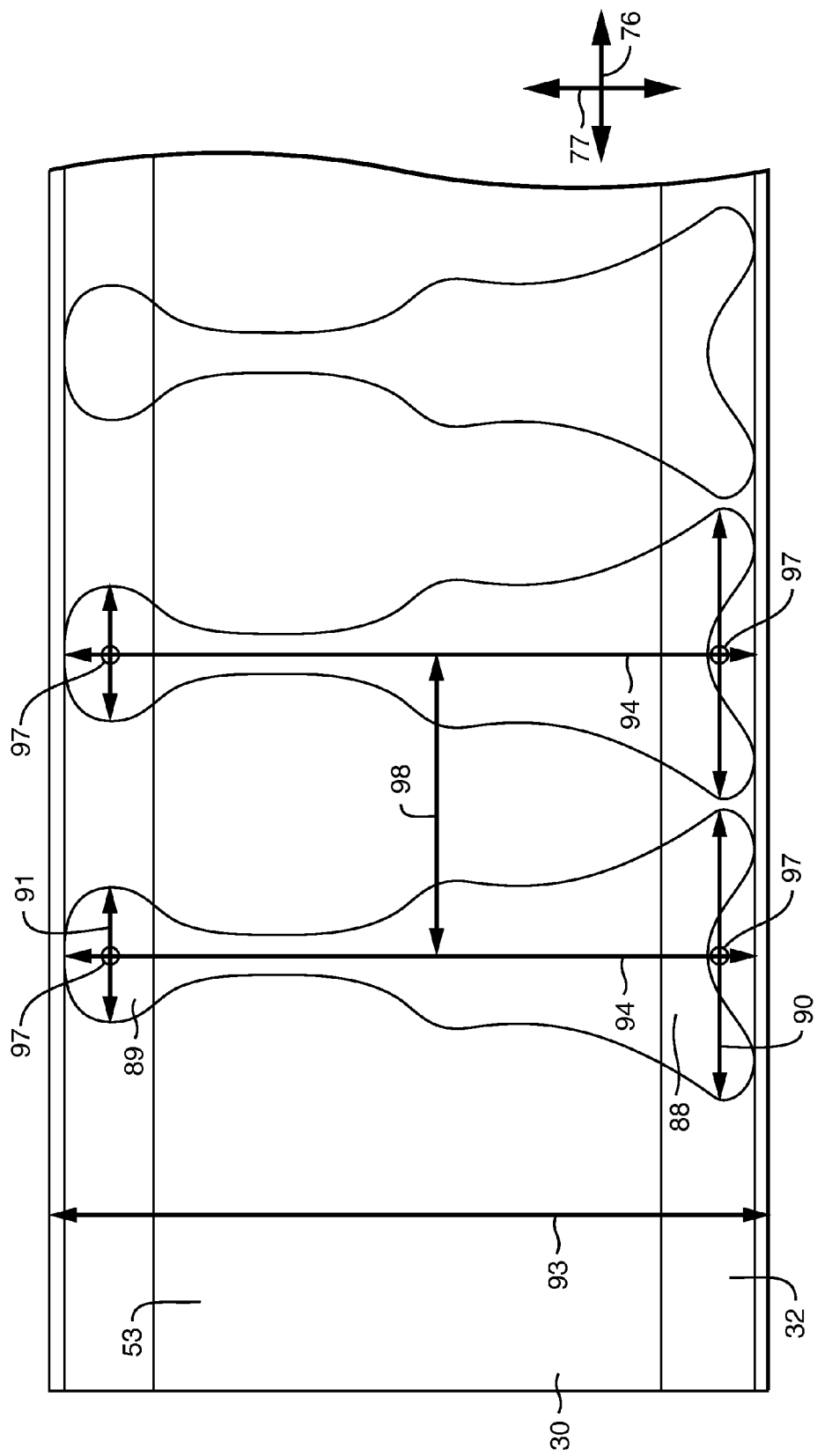
FIG. 5 is a top view of a web of body adhering absorbent articles according to still another embodiment of the present disclosure.

The body adhering absorbent articles 20 may be manufactured in either a nested or non-nested pattern. Nested patterns are particularly preferred because they reduce the amount of raw material necessary to make an article. FIG. 5 illustrates a web of non-nested body adhering absorbent articles 20 having anterior portion 88 with maximum width dimension 90 and posterior portion 89 with machine directional maximum width dimension 91. Articles 20 have a cross-machine directional dimension 94 which is a measurement of article 20 taken along the line passing through the mid-points of lines 90 and 91. Composite web 53 has a cross-machine directional width dimension 93 that is greater than or equal to dimension 94. The machine directional length of composite web material 53 needed to make one non-nested article 20 is equal to dimension 98. The area of composite web material 53 needed to make one non-nested article 20 is equal to dimension 98 multiplied by dimension 93. For example, article 20 shown in FIG. 5 has a dimension 98 of 132 mm and a dimension 93 of 314 mm. The area of composite web 53 needed to make one article 20 with this non-nested pattern is 41,448 mm$^2$. A configuration is described to be "nested" if the area of composite web material 53 needed to make one article 20 is less than dimension 90 multiplied by dimension 94. In this example dimension 90 equals 126 mm and dimension 94 equals 302 mm equaling an area of 38,052 mm$^2$.

Figure 6:
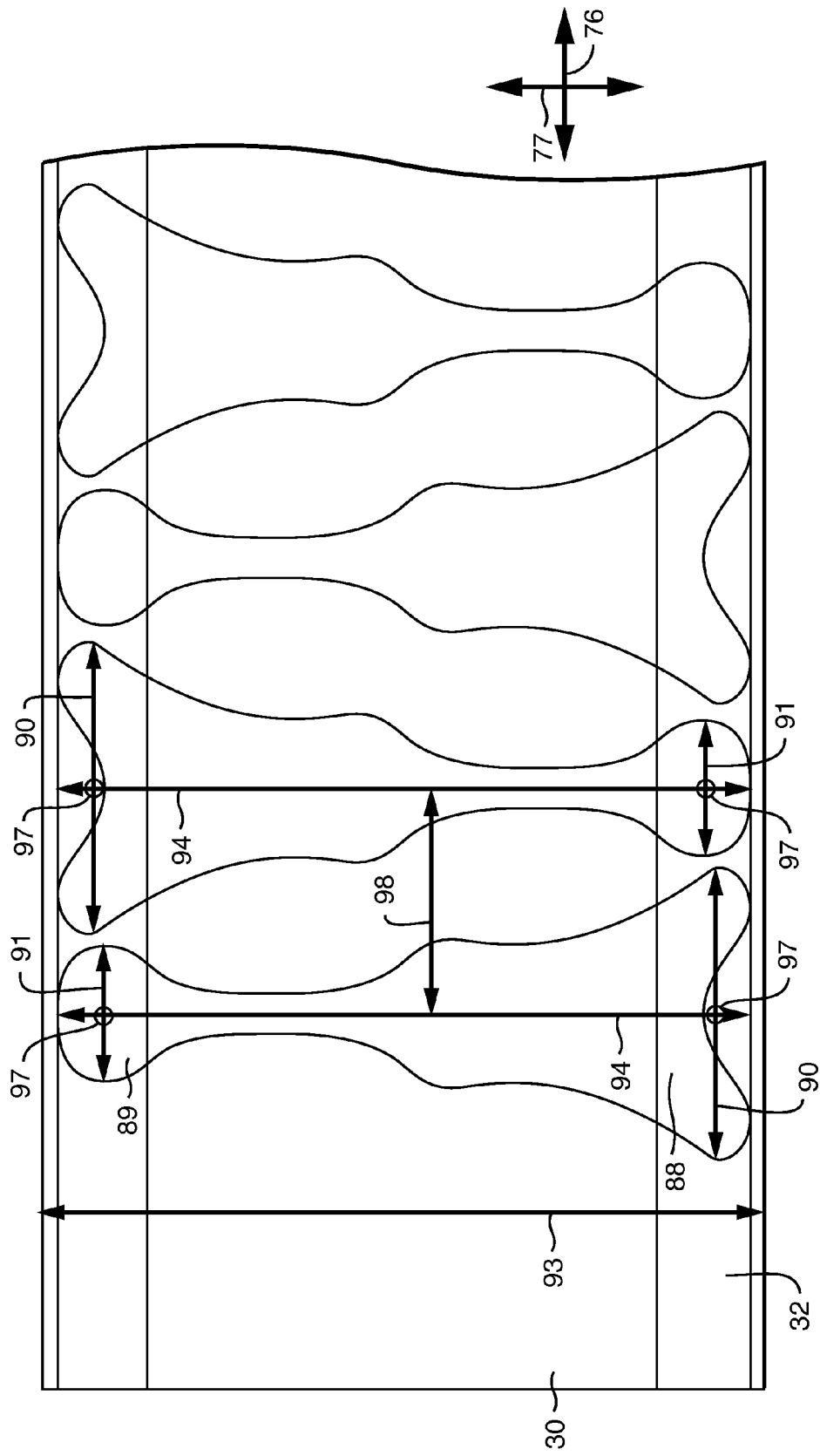
FIG. 6 is a top view of a web of body adhering absorbent articles according to still another embodiment of the present disclosure.

FIG. 6 illustrates one nested pattern of body adhering absorbent articles 20. In this embodiment the machine directional length of composite web 53 necessary to make one article 20 is equal to dimension 98 and the cross directional width of composite web material 53 needed to make one article 20 is equal to dimension 93. The area of web material 35 needed to make one nested article 20 is equal to dimension 98 multiplied by dimension 93. For example, in this drawing dimension 98 is 67 mm and dimension 93 is 379 mm. The area of composite web 35 necessary to make one article 20 is 25,393 mm$^2$ which is a reduction of 39% versus the non-nested configuration shown in FIG. 5.

Figure 7:
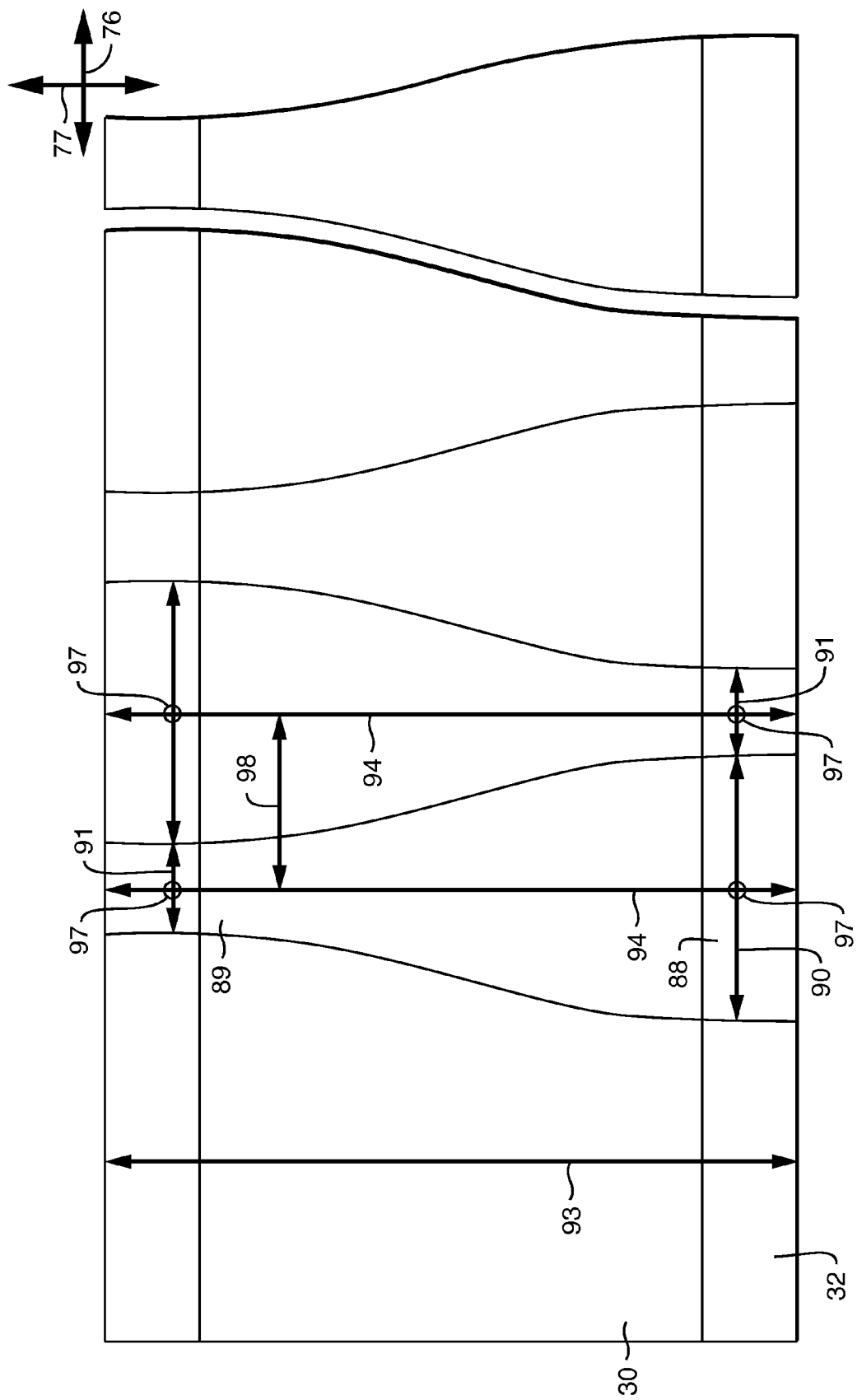
FIG. 7 is a top view of a web of body adhering absorbent articles according to still another embodiment of the present disclosure.

FIG. 7 illustrates yet another completely nested design of body adhering absorbent structure 40. The advantage of a completely nested design is that there is no trim waste to dispose of. In this embodiment the machine directional length of composite material 53 necessary to make one article 20 is equal to dimension 98 and the cross directional width of composite web material 53 needed to make one article 20 is equal to dimension 93. The area of web material 53 needed to make one nested article 20 is equal to dimension 98 multiplied by dimension 93. For example, in this drawing dimension 98 is 77 mm and dimension 93 is 303 mm. The area of composite web 53 necessary to make one article 29 is 23,331 mm$^2$ which is a reduction of 44% versus the non-nested configuration shown in FIG. 5.

Figure 8:
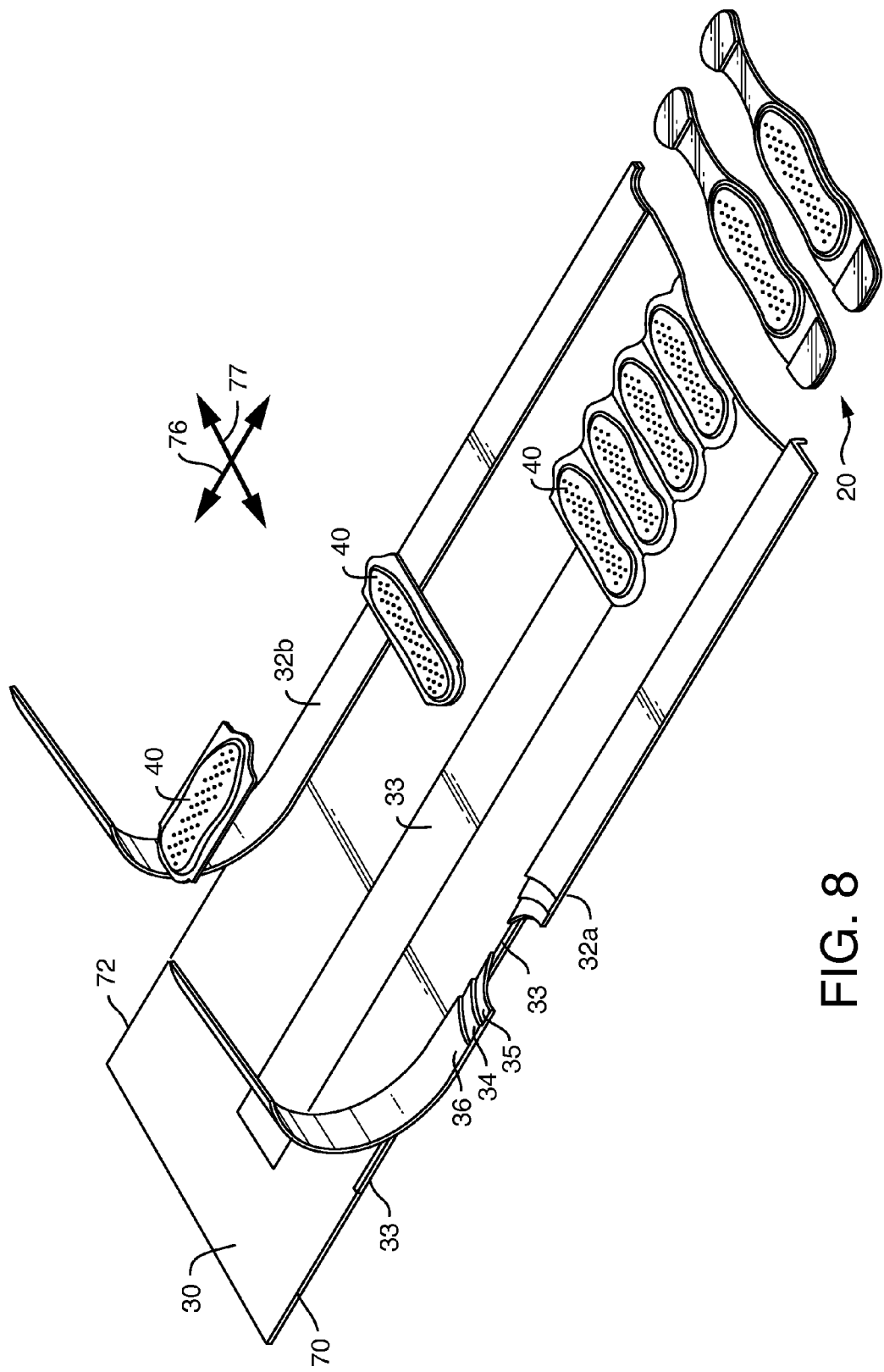
FIG. 8 shows a cross-machine direction method of manufacturing a body adhering absorbent article according to one embodiment of the present disclosure.

Now with reference to FIG. 8, one cross-machine direction method of making a body adhering absorbent article 20 having reduced curl is illustrated. In this embodiment a web of shell material 30 stretchable in the cross-machine direction 77 is provided. Components, such as adhesive transfer layers 32a and 32b are attached to the peripheral left and right edges, 70 and 72 respectively, of the shell material 30, while other components, such as an absorbent article 40 are attached to the interior portion of the shell material. Because the shell material is stretchable primarily in the cross-machine direction and since the web is not under cross-machine direction tension components that are attached to the shell web will have little or no residual stretch in the attachment regions. As a result curl is reduced or eliminated in the individual body adhering absorbent article 20.

The cross-machine stretchable web of shell material 30 is preferably stretchable from about 50 to about 200% in the cross-machine direction and less than 20% stretchable in the machine direction and more preferably from about 0 to about 10% stretchable in the machine direction. Suitable cross-machine stretchable web shell material include, for example, laminate materials that include at least one elastic film foam, woven, or nonwoven layer and a CD extensible nonwoven web such as a necked nonwoven web. The nonwoven web is preferably a spunbond web, or a laminate which includes a spunbond web. The nonwoven web is stretched or elongated in a machine direction producing necking of the web in the cross-machine direction. While in an elongated or necked position, the web is bonded to an elastic sheet to form a nonwoven laminate material that is stretchable in a direction parallel to the direction of necking of the web, and which partly or fully recovers when the stretching force is removed. The necked nonwoven web is thermally bonded to the elastic core layer. Other bonding processes may also be used including, but not limited to, pressure bonding, adhesive bonding, and ultrasonic welding.

Components such as an ATL 32 are attached to the peripheral regions of the cross-machine stretchable shell web 30. The components may be attached using any method known in the art, for example, pressure bonding, adhesive bonding, thermal bonding and ultrasonic welding. For example, as illustrated in FIG. 8, webs of ATL 32 are attached using construction adhesive 33 applied to the peripheral edges 70 and 72 of the cross-machine stretchable web shell of material 30. Once the components are attached to form a composite web 53, individual body adhering absorbent articles are die cut from the composite web 53. Upon cutting, the shell material will have little or no residual tension thus reducing or eliminating the curl in the relaxed untensioned body adhering absorbent article 20.

Figure 9:
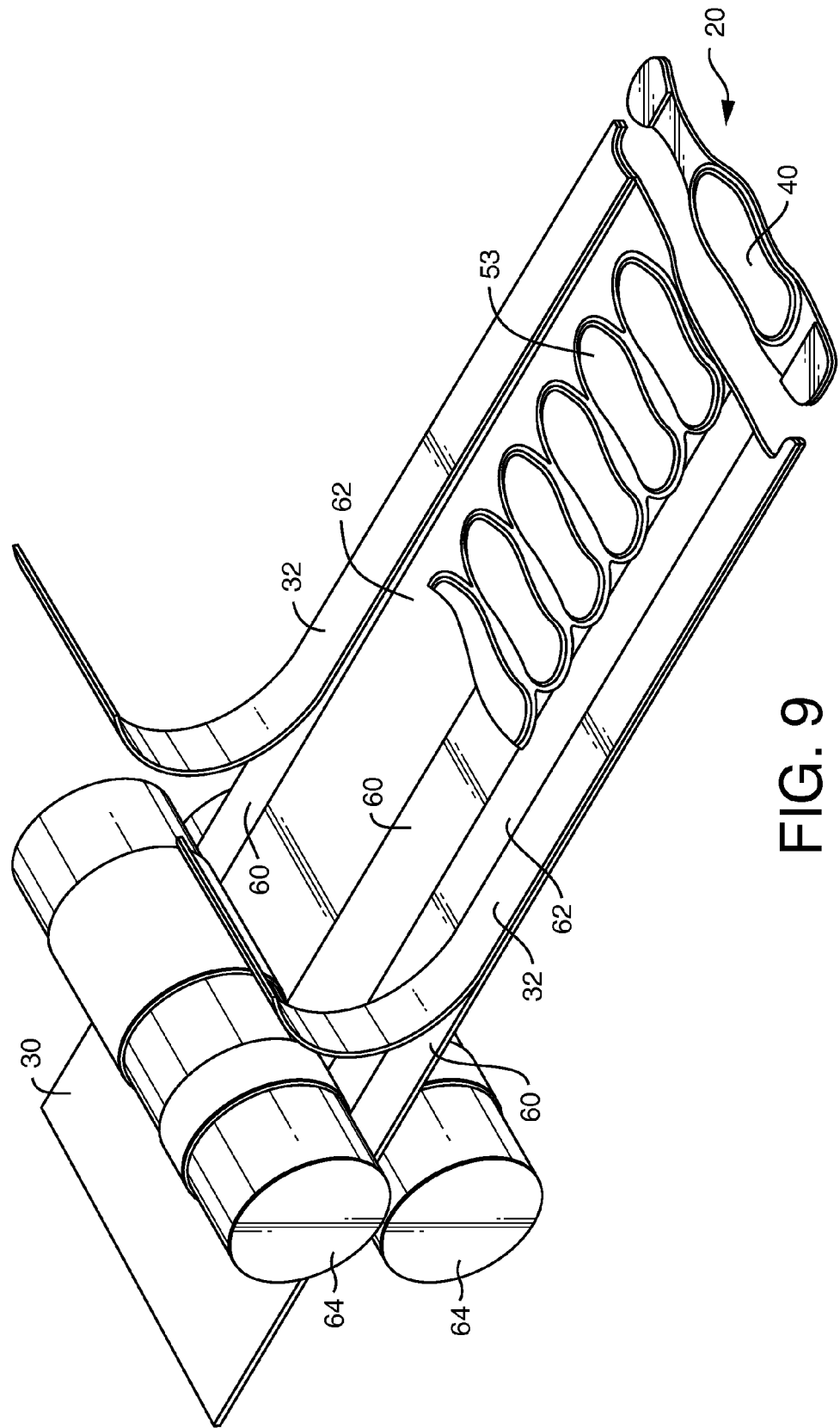
FIG. 9 shows a cross-machine direction method of manufacturing a body adhering absorbent article according to yet another embodiment of the present disclosure.

With reference to FIG. 9, another embodiment for manufacturing a body adhering absorbent article in the cross-machine direction is illustrated. As shown in FIG. 9, a web of shell material 30 is mechanically activated by mechanically treating one or more selected regions 62 of the shell web 30 in one or more selected directions, whereby the stretchability in the selected direction of the material can be controlled and substantially increased in the region(s) that have been mechanically treated. For example, the elasticity of a material with an initial stretch of from about 0 to about 25% in the cross-machine direction can be increased to about 50 to about 200% stretch with machine treatment that is orientated in the machine direction. By mechanically treating the shell material 30 an elastic web material having zoned stretching in the cross-machine direction may be produced. For example, by mechanically treating the web in a direction parallel to the machine direction, treated regions or zones of material 62 are produce, such that when a tensioning force is applied in the cross-machine direction the treated zones 62 will stretch or exhibit increased stretching, while unmachined, untreated zones 60 display little or no additional stretch.

Accordingly, a web having mechanically activated and nonactivated zones may be prepared as known in the art, for example as described in U.S. Pat. Nos. 4,834,741 and 5,366,782, the contents of which are incorporated herein in a manner consistent with the present disclosure. For example a web, such as a polyolefin apertured web or a low density polyethylene film, both of which are substantially inelastic, is longitudinally passed through rolls 64 of ring-rolling apparatus illustrated in FIG. 9 to make a web having activated and nonactivated zones. Rolls 64 consist of bands of teeth which are separated by a uniform distance from one another. The distance between the bands of teeth can be varied to create activated and nonactivated zones having varying widths and spacing.

Ring-rolling of the shell web 30 incrementally stretches and thereby plastically deforms a plurality of the beam-like elements in the transverse direction. The stretching of the beam-like elements occurs incrementally across the width of the web (transverse direction) as the film is constrained at the tips of the teeth and is stretched an amount that is proportional to the pitch and the engagement. As the engagement depth of the rolls 64 is increased, the incremental stretching and the plastic deformation of the beam-like elements are increased.

In a preferred embodiment the shell web would be a composite of outer facings webs such as spunbond, SM, SMS, or BCW that yield when passed through the ring rolling apparatus and the center core layer is an elastic film or elastic nonwoven that stretches when passing through the apparatus. After passing through the zoned ring rolling apparatus the web retracts and is elasticized in the regions where the nonwoven has been yielded.

Once activated regions 62 and nonactivated regions 60 have been formed, components such as an ATL 32 or absorbent components 40 are attached to the nonactivated regions 60 of the web. The components may be attached using any method known in the art, for example, adhesive bonding, thermal bonding and ultrasonic welding. Once the components are attached to form a composite web 53, individual body adhering absorbent articles 20 are die cut from the composite web. As a result of this configuration the components are laminated to nonactivated, non-stretchable, portions of the web so that when the individual body adhering absorbent articles 20 are die cut from the composite web there will be little or no residual stretch in the shells laminated regions where the ATL components 32 or absorbent article components 40 are attached, thereby reducing or eliminating curl in the individual body adhering absorbent article 20.

Figure 10:
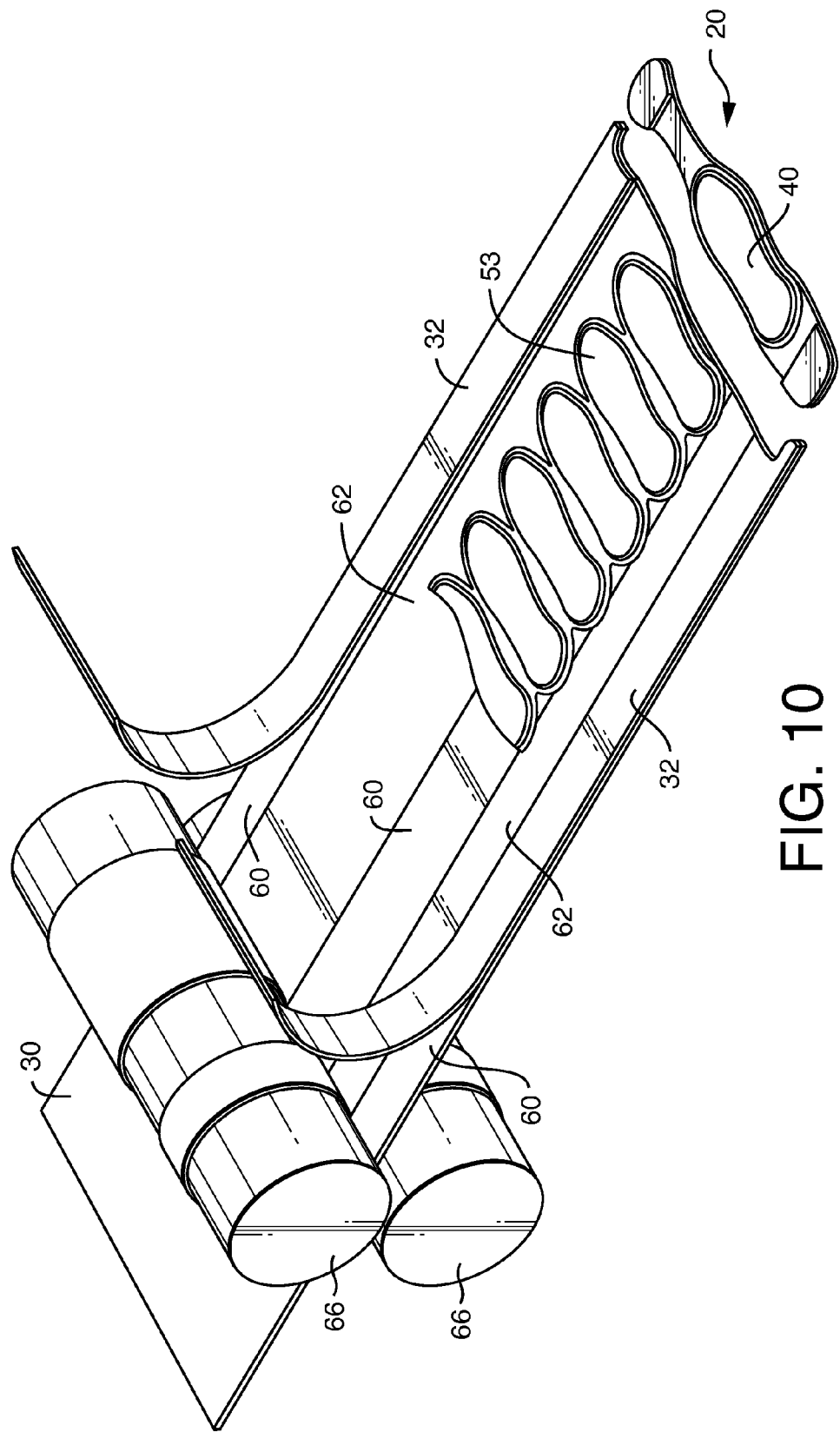
FIG. 10 shows a cross-machine direction method of manufacturing a body adhering absorbent article according to still another embodiment of the present disclosure.

Turning now to FIG. 10 another embodiment for manufacturing a body adhering absorbent article orientated in the cross-machine direction is illustrated. As shown in FIG. 10, a web 30 is activated by treating one or more selected regions 62 of the web 30 in one or more selected directions, whereby the stretchability in the selected direction of the material can be controlled and substantially increased in the selectively treated region(s). For example, the elasticity of a material with an initial stretch of from about 0 to about 25% in the cross-machine direction can be increased to about 100 to about 200% stretch with selective treatment that is orientated in the machine direction. By selectively treating the shell material 30 in the machine direction, an elastic web material having zoned stretching in the cross-machine direction may be produced. For example, by thermally treating the web in a direction parallel to the machine direction, treated regions or zones of material 62 are produced, such that when a tensioning force is applied in the cross-machine direction the treated zones 62 will stretch or exhibit increased stretching, while untreated zones 60 display little or no additional stretch.

Accordingly, in one embodiment the web of shell material 30 may comprise a latent elastic laminate that upon activation may suitably be stretched in the cross-machine direction 77 by at least about 25%, or at least about 100%, or at least about 200%, and may suitably recover at least about 5%, or at least about 15%, or about 25% of the stretched length. The latent elastic laminate materials may have a basis weight between about 2 and about 60 grams per square meter (gsm), or between about 5 and about 30 gsm, or between about 5 and about 15 gsm. Suitable latent elastic materials include, for example, the latent elastic laminate described in U.S. Pat. No. 7,820,001, the contents of which are incorporated herein in a manner consistent with the present disclosure. In a preferred embodiment the latent elastic laminate is formed as a multi-segmented film web having heat activatable regions or zones where one or more of the segments within the multi-segmented film comprises an elastic segment, any additional layers laminated thereto desirably comprise a CD extensible material or fabric. In this regard, the additional layer or layers can comprise, as examples, extensible nonwoven materials (e.g., creped nonwovens or nonwovens comprising highly crimped fibers), necked nonwovens, meshed fabrics, loosely woven fabrics, elastic composite materials and/or other like materials. Desirably the fabric comprises one or more layers of thermoplastic fibers which are elastic, inherently extensible or which have been treated so as to be become extensible and/or elastic and which also have a cloth-like hand and drape. The composition of the thermoplastic polymer may be selected as desired to achieve a material having the desired physical attributes such as, for example, elasticity, hand, tensile strength, cost and so forth. Further, the outer nonwoven layer may be treated such as, for example, by embossing, hydroentangling, neck stretching, mechanically softening, printing, anti-static treatment or treated in some other manner in order to achieve desired aesthetics and/or functional characteristics.

In one embodiment, to activate the latent elastic laminate, the laminate is heated to at least a softening point of the latent polymer. When the latent polymer softens, the elastic members are able to retract and gather the substrate, thereby resulting in a gathered structure that is elastic. Latent heat activation may be achieved at temperatures between about 70 and about 290° C., or between about 70 and about 200° C., depending largely upon the glass transition temperature of the latent polymer as well as the basis weight of the polymer and the laminate, and also depends upon the dwell time. For example, the latent heat activation may be achieved at a temperature between about 140 and about 160° C. with a dwell time of about 5 to about 10 seconds, or at a temperature between about 70 and about 160° C. with a dwell time of about 1 to about 10 seconds.

Accordingly, in one embodiment a transfer roller feeds the web 30 having heat activatable elastic zones into a heat activation unit. The heat activation unit may comprise, for example, a pair of rolls (two shown in FIGS. 10, 66 and 66). The rolls are preferably configured to provide zoned heating to the web as it travels through the nip. For example, the rolls may be configured to have both heated and unheated regions so that as the web travels through the nip it is either heated on its upper and bottom surface by the heated regions of the rolls or is subjected to little or no heating by the unheated regions of the rolls. Alternatively, the rolls may be uniformly heated but comprise raised elements, that when opposed create a heated nip that selectively activates the web. The distance of web activated, as well as the necessary residence time for heat activation to occur, may be controlled by varying the design and rotational speed of the rollers 66.

In certain preferred embodiments upon activation the web of shell material 30 is allowed to retract at ambient temperatures as it passes into and out of the heat activation unit. This retraction can occur after the web travels from a first vacuum conveyor in the heating section to any subsequent conveyor and advantageously to a subsequent vacuum conveyor in the quenching section. After this additional retraction has occurred the web may be cooled on the quench vacuum roll(s) to preserve this retracted state as the web is processed further. During heat activation, generally the web of shell material 30 can be retracted from about 15 to about 55%. Preferably the web of shell material 30 can be retracted from about 25 to about 45%. Most preferably the web of shell material 30 can be retracted about 35%. Retraction can occur between one or more of the rollers 66.

After heat activation, components such as an ATL component 32 or an absorbent article component 40 are attached to the inelastic regions 60 of the web. The components may be attached using any method known in the art, for example, adhesive bonding, thermal bonding and ultrasonic welding. Once the components are attached to form a composite web 53, individual body adhering absorbent articles 20 are die cut from the composite web 53. As a result of this configuration the components are laminated to nonactivated, non-stretchable, portions of the web so that when the individual body adhering absorbent articles 20 are die cut from the composite web 53 there will be little or no residual stretch in the shell's laminated regions which will reduce or eliminate curl in the individual body adhering absorbent articles 20.

In an alternative embodiment, individual body adhering absorbent articles 20 may be manufactured as described above, however, the components such as an ATL component 32 or absorbent article component 40 are attached to a shell web 30 having heat activatable elastic zones prior to activation. The components may be attached using any method known in the art, for example, adhesive bonding, thermal bonding and ultrasonic welding. Once the components are attached to form a composite web 53 regions between the components are heat activated. After activation, individual body adhering absorbent articles 20 are die cut from the composite web 53. As a result of this configuration the components are laminated to nonactivated, non-stretchable, portions of the web so that when the individual body adhering absorbent articles 20 are die cut from the composite web 53 there will be little or no residual stretch in the shells laminated regions which will reduce or eliminate curl in the individual body adhering absorbent article.

In yet another embodiment a body adhering absorbent article 20 may be manufactured using a multi-segmented film web having alternating elastic and inelastic regions. Exemplary multi-segmented film webs include webs prepared as described in U.S. application Ser. No. 12/649,427, filed Dec. 30, 2009, the contents of which are incorporated herein in a manner consistent with the present disclosure. For example, a multi-segmented film web may be provided having segments that stretch from about 0 to about 25% in the cross-machine direction 77 and other segments that stretch from about 50 to about 100% in the cross-machine direction 77. Preferably each segment has little or no stretch in the machine direction 76. The segments are preferably arranged such that the periphery of the web comprises segments having from about 50 to about 100% stretch in the cross-machine direction, while the interior portion of the web comprises one or more segments having from about 0 to about 25% stretch in the cross-machine direction 77.

Preferably the multi-segmented film is a laminate comprising two or more films and/or fabrics. For example, the multi-segmented film may be bonded to a nonwoven web, which may be either a single layer nonwoven web or a multilayer nonwoven laminate that includes at least one layer of a nonwoven web or multiple nonwoven layers such as, for example, a three layered laminate comprising spunbond/meltblown/spunbond. The particular composition of any additional layers attached to the multi-segmented film may be selected to achieve desired attributes such as, for example, aesthetics, strength, and durability. The multi-segmented film and other fabric(s) can be laminated together by means known to those skilled in the art such as, for example, by pressure bonding, thermal bonding, ultrasonic bonding, adhesive bonding and the like.

Where one or more of the segments within the multi-segmented film comprises an elastic segment, any additional layers laminated thereto desirably comprise a CD extensible material or fabric. In this regard, the additional layer or layers can comprise, as examples, extensible nonwoven materials (e.g., creped nonwovens or nonwovens comprising highly crimped fibers), necked nonwovens, meshed fabrics, loosely woven fabrics, elastic composite materials and/or other like materials. Desirably the fabric comprises one or more layers of thermoplastic fibers which are elastic, inherently extensible or which have been treated so as to become extensible and/or elastic and which also have a cloth-like hand and drape. The composition of the thermoplastic polymer may be selected as desired to achieve a material having the desired physical attributes such as, for example, elasticity, hand, tensile strength, cost and so forth. Further, the outer nonwoven layer may be treated such as, for example, by embossing, hydroentangling, neck stretching, mechanically softening, printing, anti-static treatment or treated in some other manner in order to achieve desired aesthetics and/or functional characteristics.

Components such as an ATL or an absorbent article are attached to the inelastic regions of the shell web. The components may be attached using any method known in the art, for example, adhesive bonding, thermal bonding and ultrasonic welding. Once the components are attached to form a composite web, individual body adhering absorbent articles are die cut from the composite web 53. As a result of this configuration the components are laminated to nonactivated, non-stretchable, portions of the web so that when the individual body adhering absorbent articles 20 are die cut from the composite web 53 there will be little or no residual stretch in the shells laminated regions which will reduce or eliminate curl in the individual body adhering absorbent article.

Figure 11:
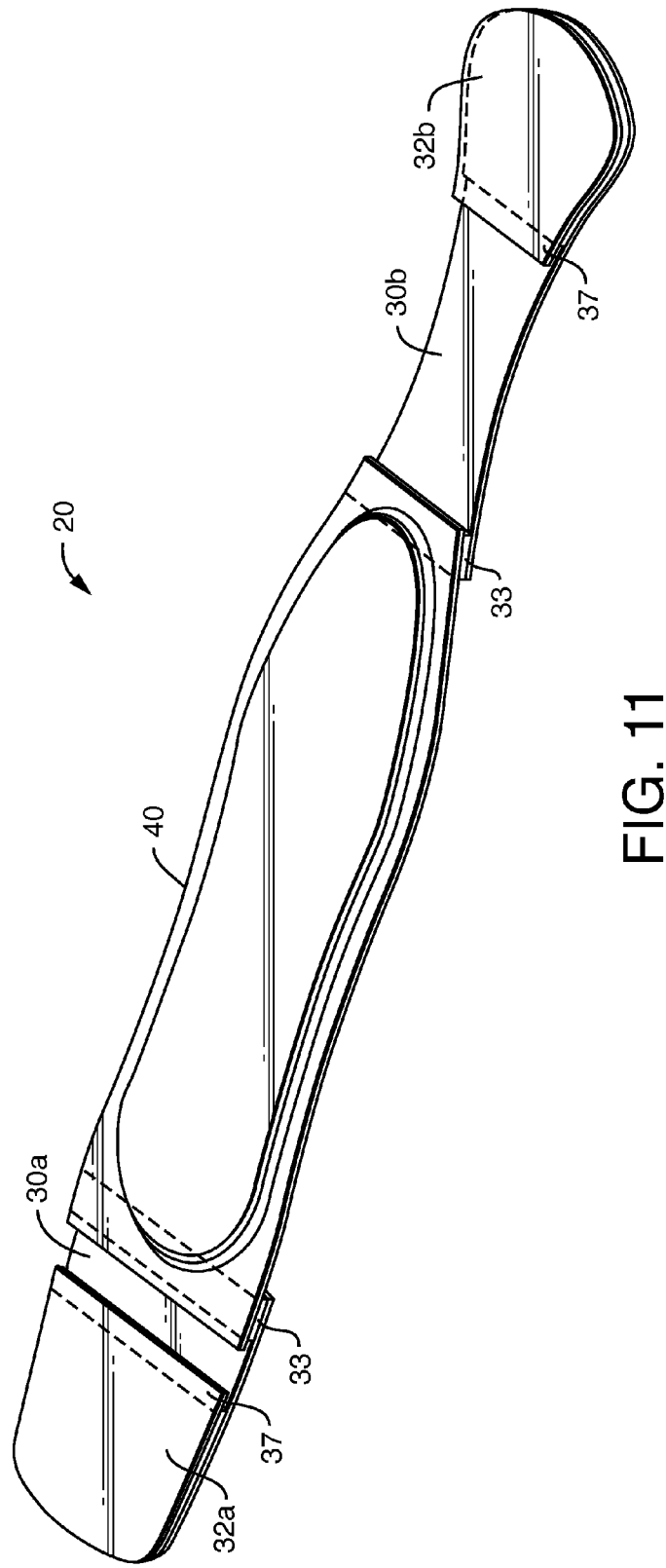
FIG. 11 is a perspective view of a body adhering absorbent article having a segmented shell for reducing curl.
Figure 12:
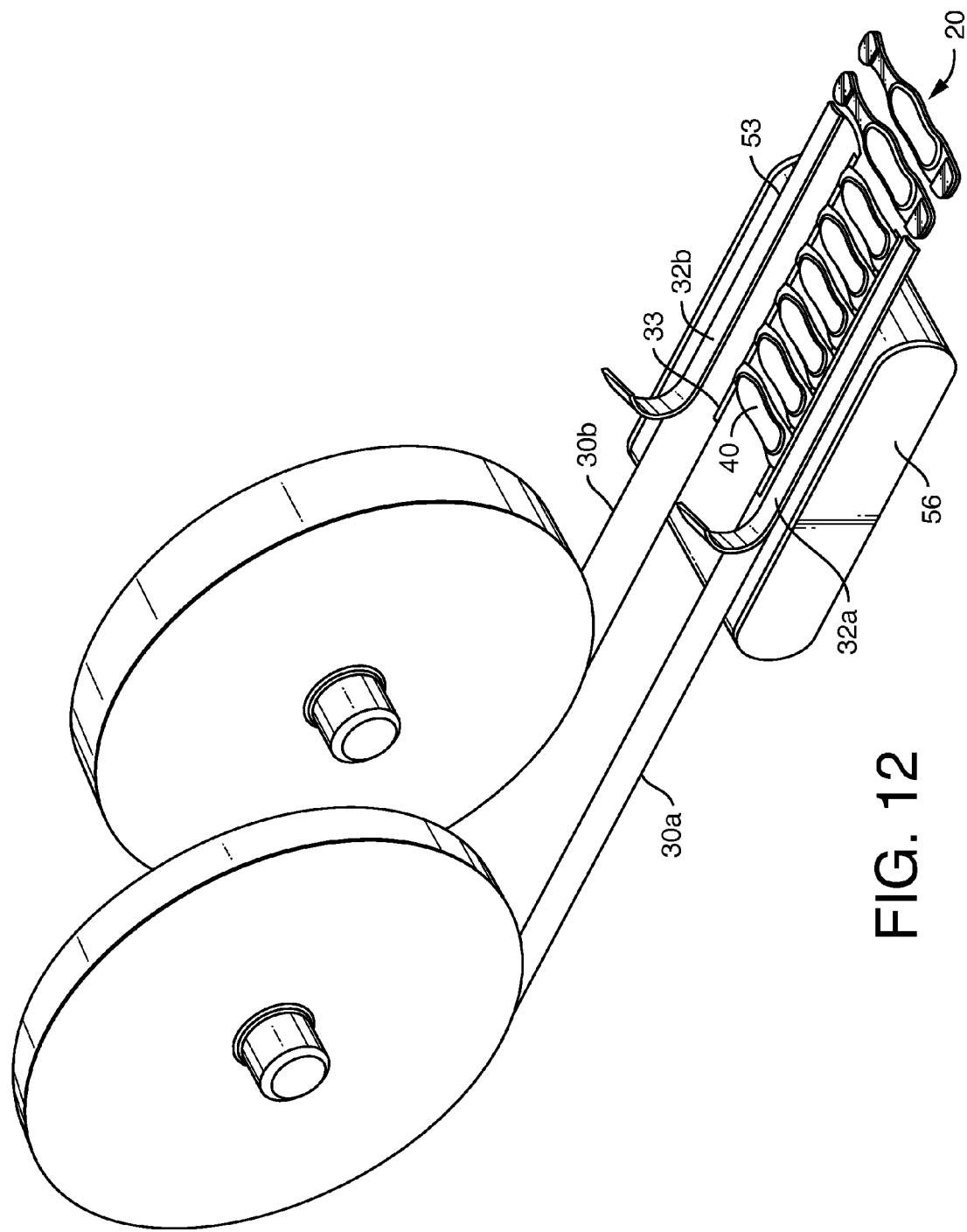
FIG. 12 shows a cross-machine direction method of manufacturing a body adhering absorbent article having a segmented shell according to yet another embodiment of the present disclosure.

Referring to FIG. 11, in still another embodiment a body adhering absorbent article 20 having a segmented shell may be manufactured to reduce curl. As illustrated in FIG. 12, a body adhering absorbent article may be manufactured by delivering two webs of CD stretchable shell material 30*a* and 30*b* such that there is a predetermined space between the inboard peripheral edges of the webs. ALT webs 32*a* and 32*b* are attached adjacent to the outboard edges of shell webs 30*a* and 30*b*. Absorbent article components 40 are then delivered and attached to the inboard peripheral edges of shell webs 30*a* and 30*b* forming composite web 53. Individual body adhering absorbent articles 20 are then die cut from the composite web 53. Because the shell material is stretchable primarily in the cross-machine direction and since the web is not under cross-machine direction tension components that are attached to the shell web 30, the shell web 30 will have little or no residual stretch in the attachment regions. As a result curl is reduced or eliminated in the individual body adhering absorbent article 20.

Figure 13:
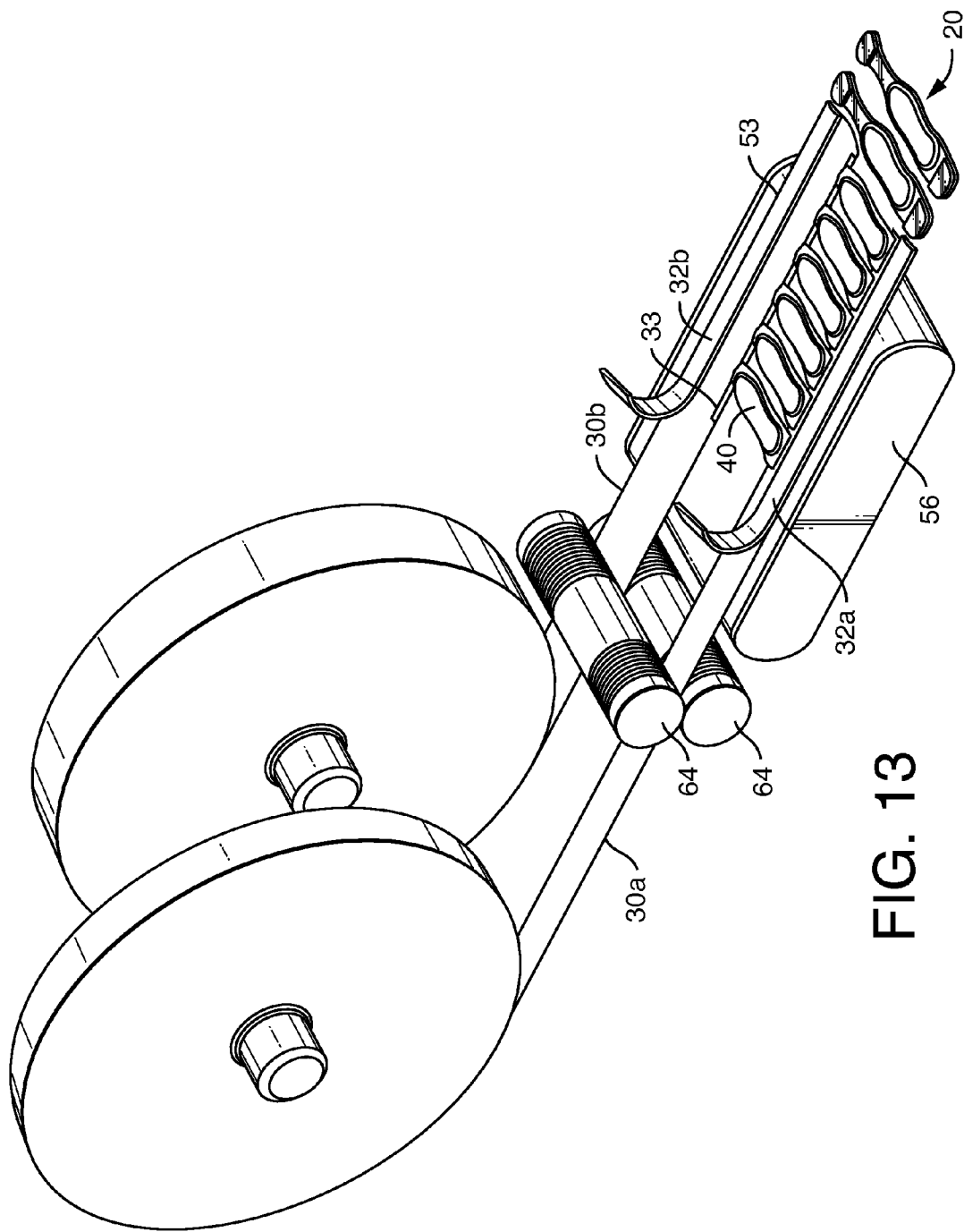
FIG. 13 shows a cross-machine direction method of manufacturing a body adhering absorbent article having a segmented shell according to yet another embodiment of the present disclosure.

Referring to FIG. 13, in still another embodiment a body adhering absorbent article 20 having a segmented shell may be manufactured to reduce curl. As illustrated in FIG. 13, a body adhering absorbent article may be manufactured by delivering two webs of activatable shell material 30*a* and 30*b* such that there is a predetermined space between the inboard peripheral edges of the webs. Shell webs 30*a* and 30*b* are then passed through an activation process, for example a mechanical activation process such as a ring rolling process previously described. ALT webs 32*a* and 32*b* are then attached adjacent to the outboard edges of activated shell webs 30*a* and 30*b*. Absorbent article components 40 are then delivered and attached to the inboard peripheral edges of activated shell webs 30*a* and 30*b* forming composite web 53. Individual body adhering absorbent articles 20 are then die cut from the composite web 53. Because the activated shell material 30 is stretchable primarily in the cross-machine direction and since the web is not under cross-machine direction tension components that are attached to the activated shell web 30, shell web 30 will have little or no residual stretch in the attachment regions. As a result curl is reduced or eliminated in the individual body adhering absorbent article 20.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

We claim:

1. A method of manufacturing body adhering absorbent articles orientated in the cross-machine direction comprising the steps of:
   a. supplying a pair of adhesive transfer layers comprising a nonwoven carrier, a body attachment adhesive, and a peel strip;
   b. supplying an elastic shell web having a longitudinal and transverse direction and a pair of opposing peripheral edges extending in the longitudinal direction;
   c. attaching the pair of adhesive transfer layers to the opposing peripheral edges of the elastic shell web;
   d. attaching at least one absorbent structure component to the shell web interior to the opposing peripheral edges to form a composite web material; and
   e. cutting the composite web material to form a body adhering absorbent article having a predetermined size and shape.

2. The method of claim 1 wherein the absorbent structure component is selected from the group consisting of a composite absorbent structure, a barrier layer, a body adhering adhesive, an absorbent and containment flaps.

3. The method of claim 1 wherein the steps of attaching comprise laminating, adhesive attachment, thermal bonding, pressure bonding or ultrasonic bonding.

4. A method of manufacturing body adhering absorbent articles orientated in the cross-machine direction comprising the steps of:
   a. supplying an activatable web of shell material having a longitudinal and transverse direction;
   b. supplying a pair of adhesive transfer layers comprising a nonwoven carrier, a body attachment adhesive, and a peel strip;
   c. intermittently activating a portion of the web of shell material in the longitudinal direction to create activated and nonactivated portions of the web of shell material in the transverse direction;
   d. attaching at least one of the pair of adhesive transfer layers to at least one nonactivated portion of the web of shell material;
   e. attaching at least one component to at least one nonactivated portion of the web of shell material to form a composite web material; and
   f. cutting the composite web material to form a body adhering absorbent article having a predetermined size and shape.

5. The method of claim 4 wherein the at least one component is selected from the group consisting of an adhesive transfer layer, an absorbent structure, a barrier layer, a body adhering adhesive, an absorbent and containment flaps.

6. The method of claim 4 wherein the activatable web of shell material is a mechanically activatable web of shell material.

7. The method of claim 6 wherein the mechanically activatable web of shell material is a composite comprising at least one inelastic material and at least one elastic material.

8. The method of claim 4 wherein the activatable web of shell material is a mechanically activatable web of shell material and the step of activating comprises mechanically activating the web of shell material by passing the web of shell material through a pair of interconnecting grooved rolls.

9. The method of claim 4 wherein the activatable web of shell material is a heat activatable web of shell material.

10. The method of claim 9 wherein the activatable web of shell material is a heat activatable web of shell material and the step of activating comprises intermittently heating the web of shell material.

11. The method of claim 9 wherein the step of activating comprises passing the web of shell material through an apparatus configured for zoned heated compression of the web of shell material.

12. The method of claim 4 wherein the step of attaching comprises laminating, adhesive attachment, thermal bonding, pressure bonding or ultrasonic bonding.

13. A method of manufacturing a body adhering absorbent article orientated in the cross-machine direction comprising the steps of:
   a. supplying a web of shell material having elastic and inelastic zones;
   b. supplying a pair of adhesive transfer layers comprising a nonwoven carrier, a body attachment adhesive, and a peel strip;
   c. attaching at least one of the pair of adhesive transfer layers to at least one of the inelastic zones of the web of shell material;
   d. attaching at least one component to the inelastic zone of the web of shell material to form a composite web material; and
   e. cutting the composite web material to form a body adhering absorbent article having a predetermined size and shape.

14. The method of claim 13 wherein the at least one component is selected from the group consisting of an absorbent structure, an adhesive transfer layer, a barrier layer, a body adhering adhesive, an absorbent and containment flaps.

15. The method of claim 13 wherein the step of attaching comprises laminating, adhesive attachment, thermal bonding, pressure bonding or ultrasonic bonding.

16. A method of manufacturing a segmented body adhering absorbent article comprising the steps of:
   a. supplying two webs of activatable shell material;
   b. activating the two webs of shell material;
   c. attaching a web comprising an adhesive transfer layer comprising a nonwoven carrier, a body attachment adhesive, and a peel strip to the two activated webs of shell material;
   d. attaching an absorbent component to the two webs of shell material to form a composite web material; and
   e. cutting the composite web material to form a segmented body adhering absorbent article having a predetermined size and shape.

17. The method of claim 16 wherein the absorbent component is selected from the group consisting of an absorbent structure, an adhesive transfer layer, a barrier layer, a body adhering adhesive, an absorbent and containment flaps.

18. The method of claim 16 wherein the activatable webs of shell material are mechanically activatable webs of shell material and the step of activating comprises mechanically activating the webs of shell material by passing the webs of shell material through a pair of interconnecting grooved rolls.

19. The method of claim 16 wherein the activatable webs of shell material are heat activatable webs of shell material and the step of activating comprises intermittently heating the webs of shell material.

20. The method of claim 16 wherein the step of attaching the absorbent component comprises laminating, adhesive attachment, thermal bonding, pressure bonding or ultrasonic bonding.

* * * * *